US008415302B2

(12) United States Patent
Murray et al.

(10) Patent No.: US 8,415,302 B2
(45) Date of Patent: Apr. 9, 2013

(54) SURGICAL APPLICATIONS FOR BMP BINDING PROTEIN

(75) Inventors: Samuel S. Murray, Saugus, CA (US); Elsa J. Brochmann-Murray, Saugus, CA (US); Keyvan Behnam, Simi Valley, CA (US); Jeffrey C. Wang, Sherman Oaks, CA (US)

(73) Assignees: The Regents of the University of California, Oakland, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 12/448,497

(22) PCT Filed: Dec. 26, 2007

(86) PCT No.: PCT/US2007/026315
§ 371 (c)(1),
(2), (4) Date: Feb. 16, 2010

(87) PCT Pub. No.: WO2008/079400
PCT Pub. Date: Jul. 3, 2008

(65) Prior Publication Data
US 2010/0183719 A1  Jul. 22, 2010

Related U.S. Application Data

(63) Continuation-in-part of application No. 11/985,745, filed on Nov. 16, 2007, now Pat. No. 8,193,312, which is a continuation-in-part of application No. 10/587,313, filed as application No. PCT/US2005/002722 on Jan. 28, 2005, now Pat. No. 8,188,219.

(60) Provisional application No. 60/876,821, filed on Dec. 22, 2006, provisional application No. 60/539,903, filed on Jan. 28, 2004.

(51) Int. Cl.
*A61K 38/10* (2006.01)
*A61K 38/12* (2006.01)
*A61K 38/18* (2006.01)
*C07K 4/12* (2006.01)
*C07K 5/12* (2006.01)
*C07K 14/51* (2006.01)
*C07K 14/495* (2006.01)

(52) U.S. Cl. ......... 514/16.7; 514/8.8; 514/8.9; 424/426; 530/317; 530/326

(58) Field of Classification Search ........................ None
See application file for complete search history.

(56) References Cited

U.S. PATENT DOCUMENTS

| 4,789,732 A | 12/1988 | Urist |
| 4,843,063 A | 6/1989 | Seyedin et al. |
| 5,393,739 A | 2/1995 | Bentz et al. |
| 5,620,867 A * | 4/1997 | Kiefer et al. ................. 435/69.4 |
| 5,981,483 A | 11/1999 | Dennis et al. |
| 6,200,606 B1 | 3/2001 | Peterson et al. |
| 6,291,428 B1 | 9/2001 | Macauley et al. |
| 6,311,690 B1 | 11/2001 | Jefferies |
| 6,322,786 B1 | 11/2001 | Anderson |
| 2003/0095993 A1 | 5/2003 | Bentz et al. |
| 2007/0056050 A1 | 3/2007 | Clokie et al. |
| 2007/0065415 A1 | 3/2007 | Kleinsek et al. |
| 2008/0241108 A1 | 10/2008 | Murray et al. |
| 2008/0268012 A1 | 10/2008 | Behnam et al. |
| 2009/0047360 A1 | 2/2009 | Murray et al. |

FOREIGN PATENT DOCUMENTS

| EP | 0409472 A1 | 1/1991 |
| JP | 4235197 | 8/1992 |
| JP | 5085939 | 4/1993 |
| JP | H09505305 | 5/1997 |
| WO | WO 96/21006 * | 7/1996 |
| WO | WO97/31661 A1 | 9/1997 |
| WO | WO97/40137 A1 | 10/1997 |
| WO | WO2004/004630 A2 | 1/2004 |
| WO | WO2004/013294 A2 | 2/2004 |
| WO | WO2004/097424 A1 | 11/2004 |
| WO | WO2005/072403 A2 | 8/2005 |
| WO | WO 2005/072403 A2 * | 8/2005 |
| WO | WO2006/093545 A1 | 9/2006 |
| WO | WO2008/079400 A2 | 8/2008 |

OTHER PUBLICATIONS

Bowie et al. Deciphering the message in protein sequences: tolerance to amino acid substitutions. Science, (Mar. 16, 1990) 247 (4948) 1306-10.*

Ngo et al., in the Protein Folding Problem and Tertiary Structure Prediction, Merz and Le Grand (Eds), Aug. 1994, Springer Verlag, pp. 433 and 492-495.*

Behnam, et al. "Alkali-urea Extraction of Demineralized Bone Matrix Removes Noggin, an Inhibitor of Bone Morphogenetic Proteins." Connective Tissue Research 2004, vol. 45, No. 4-5, pp. 257-260 (Jul. 2004).

Sampath, et al. "Dissociative Extraction and Reconstitution of Extracellular Matrix Components involved in Local Bone Differentiation." Proceedings of the National Academy of Sciences of USA, vol. 78, No. 12, pp. 7599-7603 (Dec. 1981).

Takahashi "[Bone Morphogenetic Protein (BMP): From Basic Studies to Clinical Approaches]." Nippon Yakurigaku Zasshi. Folia Pharmacologica Japonica, vol. 116, No. 4, pp. 232-240 (Oct. 2000).

Ripamonti, et al. "Xenogeneic Osteogenin a Bone Morphogenetic Protein and Demineralized Bone Matrices Including Human Induce Bone Differentiation in Athymic Rats and Baboons." Matrix: Collagen and Related Research, vol. 11, No. 6, pp. 404-411 (Jan. 1991).

Chen, et al. "Bone Morphogenetic Proteins" Growth Factors, vol. 22, No. 4, pp. 233-241 (Dec. 2004).

(Continued)

Primary Examiner — David Romeo
(74) Attorney, Agent, or Firm — McDermott Will & Emery LLP

(57) ABSTRACT

The present invention relates to the clinical application of BBP, alone or in combination with other growth factors, for use in bone healing applications, such as spinal surgery. Additional applications include use in orthopedic implantable prostheses and implantation into other surgical sites (e.g., surgical reconstruction, regional osteopenia, etc.) where bone is desired.

22 Claims, 11 Drawing Sheets

OTHER PUBLICATIONS

Supplementary European Search Report for EP05857032 dated Aug. 7, 2009.

Behnam, et al. "Identification of the Molecular Chaperon Alpha B-Crystallin in Demineralized Bone Powder and Osteoblast-Like Cells." Journal of Orthopaedic Research, vol. 20(6), pp. 1190-1196 (Nov. 2002).

Behnam, et al. "BMP Binding Peptide: a BMP-2 Enhancing Factor Deduced From the Sequence of Native Bovine Bone Morphogenetic Protein/Non-Collagenous Protein." Journal of Orthopaedic Research, vol. 23, pp. 175-180 (2005).

Brown, et al. "Friends and Relations of the Cystatin Superfamily—new members and Their Evolution." Protein Science, vol. 6, pp. 5-12 (1987).

Carano, et al. "Angiogenesis and Bone Repair." Drug Discovery Today, vol. 8(21), pp. 980-989 (Nov. 2003).

Demetriou, et al. "Fetuin/α2-HS Glycoprotein Is a Transforming Growth Factor-β Type II Receptor Mimic and Cytokin Antagonist." Journal of Biological Chemistry, vol. 271(22), pp. 12755-12761 (May 1996).

Hu, et al. "Isolation and Molecular Cloning of a Novel Bone Phosphoprotein Related in Sequence to the Cystatin Family of Thiol Protease Inhibitors." Journal of Biological Chemistry, vol. 270(1), pp. 431-436 (Jan. 1995).

Miller-Bertoglio, et al. "Maternal and Zygotic Activity of the Zebrafish ogon Locus Antagonizes BMP Signaling." Developmental Biology, vol. 214, pp. 72-89 (1999).

Murray, et al. "Strain-Dependent Differences in Vertebral Bone Mass, Serum Osteocalcin, and Calcitonin in Calcium-Replete and -Deficient Mice." Pro. Soc. Exp. Biol.. Med., vol. 203, pp. 64-73 (1993).

Notredame, et al. "T-Coffee: A Novel Method for Fast and Accurate Multiple Sequence Alignment." Journal of Molecular Biology, vol. 302, pp. 205-217 (2000).

Parfitt, et al. "Bone Histomorphometry: Standardization of Nomenclature, Symbols, and Units." Journal of Bone and Mineral Research, vol. 2(6) pp. 595-610 (1987).

Ten Dijke, et al. "Controlling Cell Fate by Bone Morphogenetic Protein Receptors." Molecular and Cellular Endrocrinology. vol. 211, pp. 105-113 (2003).

Urist, "Bone: Formation by Autoinduction." Science, vol. 150, pp. 893-899 (Nov. 1965).

Urist, "Emerging Concepts of Bone Morphogenetic Protein." Fundamentals of Bone Growth: Methodology and Applications, pp. 189-198 (1991).

Urist, et al. "Preparation and Bioassay of Bone Morphogenic Protein and Polypeptide Fragments." Methods in Enzymology, vol. 146, pp. 294-312 (1987).

Urist, et al. "Purification of Bovine Bone Morphogenetic Protein by Hydroxyapatite Chromatography." Proc.Natl. Acad. Sci. USA, vol. 81, pp. 371-375 (Jan. 1984).

Urist, et al. "Hydroxyapatite Affinity, Electroelution, and Radioimmunoassay for Identification of Human and Bovine Bone Morphogenetic Proteins and Polypeptides." Development and Diseases of Cartilage and Bone Matrix, pp. 149-176 (1987).

Zhoa, et al. "Targeted Overexpression of Insulin-Like Growth Factor I to Osteoblasts of Transgenic Mice: Increased Trabecular Bone Volume Without Increased Osteoblast Proliferation." Endocrinology, vol. 141(7), pp. 2674-2682 (2000).

International Search Report for PCT/US2005/002722 dated Dec. 19, 2005.

International Search Report for PCT/US2005/043215 dated Aug. 3, 2006.

International Search Report for PCT/US2007/026315 dated Jun. 17, 2008.

Guo et al. "Protein tolerance to random amino acid change." Proc. Natl. Acad. Sci. U.S.A. Jun. 22, 2004;101 (25):9205-10.

Murray et al. Recombinant expression, isolation, and proteolysis of extracellular matrix-secreted phosphoprotein-24 kDa. Connect Tissue Res. 2007;48(6):292-9.

Written Opinion for PCT/US2005/002722 dated Dec. 19, 2005.
Written Opinion for PCT/US2005/043215 dated Aug. 3, 2006.
Written Opinion for PCT/US2007/026315 dated Jun. 17, 2008.

* cited by examiner

```
              107
SEQ ID No 1:  Cys-Arg-Ser-Thr-Val-Arg-Met-Ser-Ala-Glu-Gln-Val-Gln-Asn-Val-Trp-Val-Arg-Cys
SEQ ID No 2:  TGC-AGA-AGC-ACC-GTG-CGG-ATG-TCT-GCT-GAA-CAG-GTG-CAG-AAC-GTG-TGG-GTT-CGC-TGC
                                                                                        126
```

FIG. 1A leader sequence    BMP-2 homology region
                           cystatin homology region
(1) MAMKMLVIFVLGMNHWTCTGFPVYDYDPASLKEALSASVAKVNSQSLSPYLFRAFRSSVKRVNALDEDSLTMDLE (75)

cystatin homology region
                         TGF-β receptor II homology region
(76) FRIQETTCRRESEADPATCDFQRGYHVPVAVCRSTVRMSAEQVQNVWVRCHWSSSSGSSSEEMFFGDILGSSTS (150)

(151) RNSYLLGLTPDRSRGEPLYEPSREMRRNFPLGNRRYSNPWPRARVNPGFE (200)    SEQ ID No 5

| human BMP-2 | F | P | L | A | D | H | L | N | S | T | N | H | A | I | V | Q | T | L | V | N | S | V | N | S | K | SEQ ID NO 6 |
|---|---|---|---|---|---|---|---|---|---|---|---|---|---|---|---|---|---|---|---|---|---|---|---|---|---|---|
| human BMP-2 | F | P | V | Y | D | Y | D | P | A | S | L | K | E | A | L | S | A | S | V | A | K | V | N | S | Q | SEQ ID NO 7 |
|  | - | - | c | - | - | - | - | c | c | - | c | - | - | - | - | c | - | c | c | - | - | c | - | c | - |  |

FIG. 3

| bovine fetuin | 114 | C | D | I | H | V | L | K | Q | D | G | Q | F | S | V | L | F | T | K | C | SEQ ID NO 8 |
|---|---|---|---|---|---|---|---|---|---|---|---|---|---|---|---|---|---|---|---|---|---|
| human TGF-β receptor II | 84 | C | - | * | V | A | V | W | R | K | N | D | E | N | I | T | L | E | T | V | C | SEQ ID NO 9 |
|  |  | - | - | - | c | - | c | c | c | c | c | c | - | c | c | c | - | - | c | - |  |
| human TGF-β receptor II | 84 | C | V | A | V | W | R | K | N | D | * | * | E | N | I | T | L | E | T | V | C | SEQ ID NO 9 |
| bovine BBP |  | C | R | S | T | V | R | M | S | A | E | Q | V | N | V | W | R | * | * | C | SEQ ID NO 10 |
|  |  | - | - | - | c | - | c | - | c | c | c | - | c | c | c | c | c | - | - | - |  |

FIG. 4
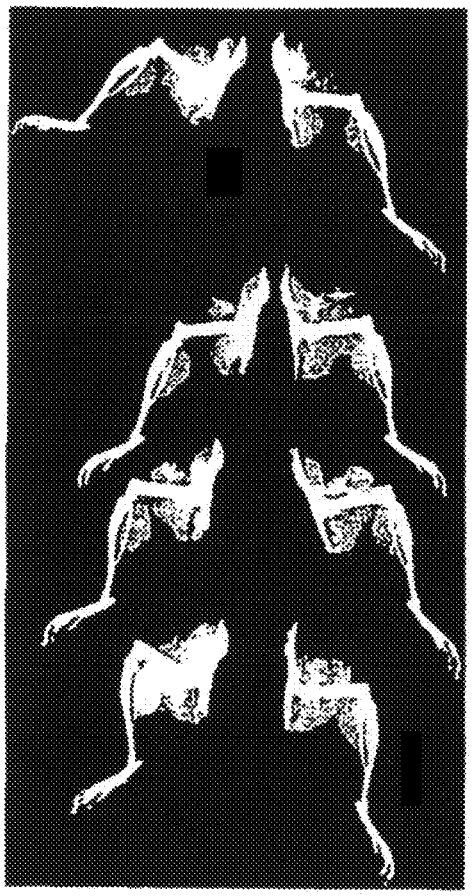
FIG. 6
FIG. 5
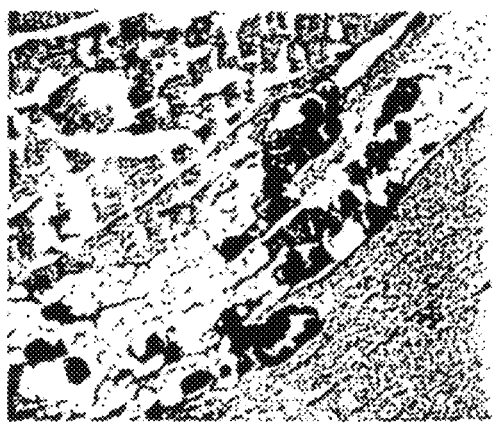

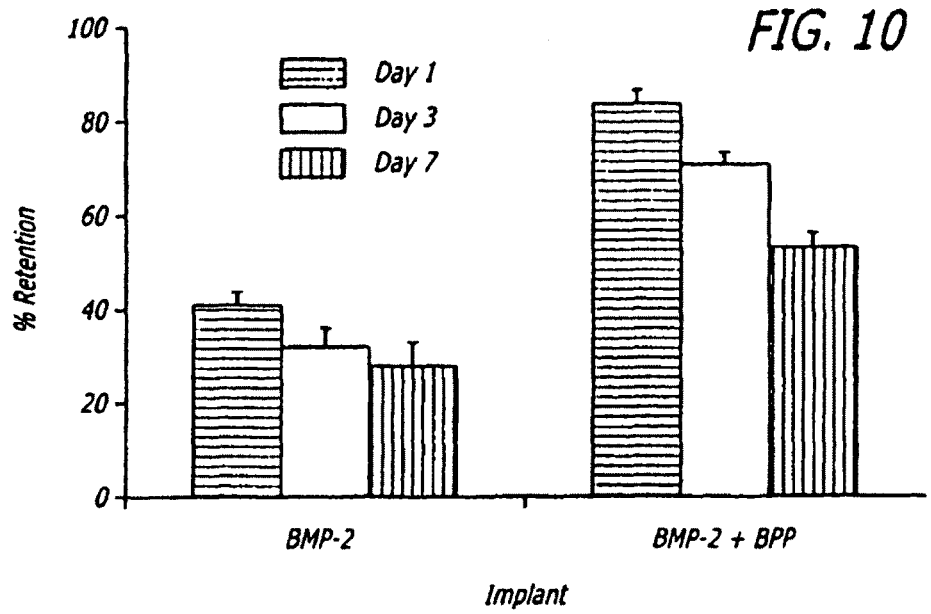
FIG. 10
FIG. 11
IQETTCRRESEADPATCDFQRGYHVPVAVCRSTVRMSAEQV (SEQ ID No 3)
CGEPLYEPSREMRRN" (SEQ ID NO 4 (SEQ ID No 4)
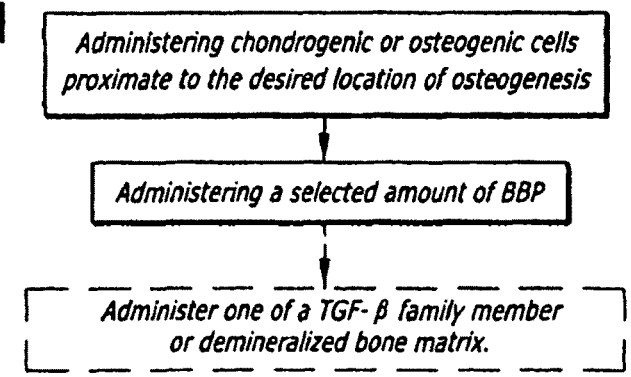
FIG. 12A

FIG. 14A

| Species | Position/Amino acid | 1 | 2 | 3 | 4 | 5 | 6 | 7 | 8 | 9 | 10 | 11 | 12 | 13 | 14 | 15 | 16 | 17 | 18 | 19 | SEQ ID No. |
|---|---|---|---|---|---|---|---|---|---|---|---|---|---|---|---|---|---|---|---|---|---|
| Consensus | | C | R | S | T | V | X | Y | S | X | X | X | V | X | X | V | X | Y | Y | C | 11a |
| Bovine | | C | R | S | T | V | R | M | S | A | E | Q | V | Q | N | V | W | V | R | C | 1a |
| Human | | C | R | S | T | V | K | V | S | A/V* | Q | Q | V | Q | G | V | H | A | R | C | 12a |
| Porcine | | C | R | S | T | V | Q | I | S | A | E | K | V | Q | D | V | W | V | R | C | 13a |
| Ovine | | C | R | S | T | V | R | M | S | A | E | R | V | Q | D | V | W | V | R | C | 14a |
| Rat | | C | R | S | T | V | Q | M | S | K | G | Q | V | K | D | V | W | A | H | C | 15a |
| Mouse | | C | R | S | T | V | Q | M | S | K | G | Q | V | K | D | V | W | A | H | C | 16a |
| Chicken | | C | K | S | V | V | E | V | S | S | E | Q | I | V | N | V | I | V | R | C | 17a |
| Salmon | | C | T | A | R | V | R | V | T | A | E | F | T | Q | V | V | S | L | N | C | 18a |
| Trout | | C | T | A | R | V | R | V | T | A | E | L | T | Q | V | V | S | L | N | C | 19a |

* The amino acid at position 9 can be either A or V.

FIG. 14B

SEQ ID No. 11b: TGC AGA AGC ACC GTG XXX YYY TCT XXX XXX XXX GTG XXX TTT TTT TGC

SEQ ID No. 12b: TGC AGA AGC ACC GTG AAG GTA TCT GCC CAG CAG GTG CAG GGC GTG CAT GCT GCT CGC TGC

SEQ ID No. 13b: TGC AGA AGC ACC GTG CAG ATA TCT GCT GAG AAG GTG CAG GAT GTG TGG GTG CGT TGT

SEQ ID No. 14b: TGC AGA AGC ACC GTG CGG ATG TCT GCT GAA CGC GTG CAG GAC GTG TGG GTT CGC TGC

SEQ ID No. 15b: TGC AGG AGC ACA GTG CAG ATG TCC AAG GGA CAG GTG AAG GAT GTG TGG GCT CAC TGC

SEQ ID No. 16b: TGC AGG AGC ACT GTG CAG ATG TCC AAG GGA CAG GTA AAG GAT GTG TGG GCT CAC TGC

SEQ ID No. 17b: TGC AAA AGC GTT GTA GAA GTC TCC AGT GAG CAG ATT GTG AAT GTT ATT GTG CGA TGC

SEQ ID No. 18b: TGC ACC GCA CGT GTT CGC GTC ACT CAG GAG TTC ACT CAG GTT GTC TCC CTG AAC TGT

SEQ ID No. 19b: TGC ACC GCA CGT GTT CGT GTC ACT CAG GTT GTC TCC CTG AAC TGT

SEQUENCE LISTING

```
<160> NUMBER OF SEQ ID NOS: 33

<210> SEQ ID NO 1
<211> LENGTH: 19
<212> TYPE: PRT
<213> ORGANISM: Bos sp.

<400> SEQUENCE: 1

Cys Arg Ser Thr Val Arg Met Ser Ala Glu Gln Val Gln Asn Val Trp
  1               5                  10                  15

Val Arg Cys

<210> SEQ ID NO 2
<211> LENGTH: 57
<212> TYPE: DNA
<213> ORGANISM: Bos sp.
<220> FEATURE:
<221> NAME/KEY: CDS
<222> LOCATION: (1)..(57)

<400> SEQUENCE: 2 tgc aga agc acc gtg cgg atg tct gct gaa cag gtg cag aac gtg tgg      48
Cys Arg Ser Thr Val Arg Met Ser Ala Glu Gln Val Gln Asn Val Trp
  1               5                  10                  15 gtt cgc tgc                                                          57
Val Arg Cys <210> SEQ ID NO 3
<211> LENGTH: 41
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 3

Ile Gln Glu Thr Thr Cys Arg Arg Glu Ser Glu Ala Asp Pro Ala Thr
1               5                   10                  15

Cys Asp Phe Gln Arg Gly Tyr His Val Pro Val Ala Val Cys Arg Ser
            20                  25                  30

Thr Val Arg Met Ser Ala Glu Gln Val
        35                  40

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Cys Gly Glu Pro Leu Tyr Glu Pro Ser Arg Glu Met Arg Arg Asn
1               5                   10                  15

<210> SEQ ID NO 5
<211> LENGTH: 200
<212> TYPE: PRT
<213> ORGANISM: Bos sp.

<400> SEQUENCE: 5

Met Ala Met Lys Met Leu Val Ile Phe Val Leu Gly Met Asn His Trp
1               5                   10                  15

Thr Cys Thr Gly Phe Pro Val Tyr Asp Tyr Asp Pro Ala Ser Leu Lys
            20                  25                  30

Glu Ala Leu Ser Ala Ser Val Ala Lys Val Asn Ser Gln Ser Leu Ser
        35                  40                  45

Pro Tyr Leu Phe Arg Ala Phe Arg Ser Ser Val Lys Arg Val Asn Ala
    50                  55                  60

Leu Asp Glu Asp Ser Leu Thr Met Asp Leu Glu Phe Arg Ile Gln Glu
65                  70                  75                  80

Thr Thr Cys Arg Arg Glu Ser Glu Ala Asp Pro Ala Thr Cys Asp Phe
                85                  90                  95

Gln Arg Gly Tyr His Val Pro Val Ala Val Cys Arg Ser Thr Val Arg
            100                 105                 110

Met Ser Ala Glu Gln Val Gln Asn Val Trp Val Arg Cys His Trp Ser
        115                 120                 125

Ser Ser Gly Ser Ser Ser Glu Glu Met Phe Phe Gly Asp Ile
    130                 135                 140

Leu Gly Ser Ser Thr Ser Arg Asn Ser Tyr Leu Leu Gly Leu Thr Pro
145                 150                 155                 160

Asp Arg Ser Arg Gly Glu Pro Leu Tyr Glu Pro Ser Arg Glu Met Arg
                165                 170                 175

Arg Asn Phe Pro Leu Gly Asn Arg Tyr Ser Asn Pro Trp Pro Arg
            180                 185                 190

Ala Arg Val Asn Pro Gly Phe Glu
        195                 200

<210> SEQ ID NO 6
<211> LENGTH: 25
<212> TYPE: PRT
<213> ORGANISM: Homo sapiens

-continued

<400> SEQUENCE: 6

Phe Pro Leu Ala Asp His Leu Asn Ser Thr Asn His Ala Ile Val Gln
1               5                   10                  15

Thr Leu Val Asn Ser Val Asn Ser Lys
            20                  25

<210> SEQ ID NO 7
<211> LENGTH: 25
<212> TYPE: PRT
<213> ORGANISM: Homo sapiens

<400> SEQUENCE: 7

Phe Pro Val Tyr Asp Tyr Asp Pro Ala Ser Leu Lys Glu Ala Leu Ser
1               5                   10                  15

Ala Ser Val Ala Lys Val Asn Ser Gln
            20                  25

<210> SEQ ID NO 8
<211> LENGTH: 19
<212> TYPE: PRT
<213> ORGANISM: Bos sp.

<400> SEQUENCE: 8

Cys Asp Ile His Val Leu Lys Gln Asp Gly Gln Phe Ser Val Leu Phe
1               5                   10                  15

Thr Lys Cys

<210> SEQ ID NO 9
<211> LENGTH: 18
<212> TYPE: PRT
<213> ORGANISM: Homo sapiens

<400> SEQUENCE: 9

Cys Val Ala Val Trp Arg Lys Asn Asp Glu Asn Ile Thr Leu Glu Thr
1               5                   10                  15

Val Cys

<210> SEQ ID NO 10
<211> LENGTH: 19
<212> TYPE: PRT
<213> ORGANISM: Bos sp.

<400> SEQUENCE: 10

Cys Arg Ser Thr Val Arg Met Ser Ala Glu Gln Val Gln Asn Val Trp
1               5                   10                  15

Val Arg Cys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (6)..(6)
<223> OTHER INFORMATION: Semi-conservative amino acid
<220> FEATURE:
<221> NAME/KEY: MOD_RES
<222> LOCATION: (7)..(7)
<223> OTHER INFORMATION: Conservative amino acid
<220> FEATURE:
<221> NAME/KEY: MOD_RES

```
<222> LOCATION: (9)..(11)
<223> OTHER INFORMATION: Semi-conservative amino acid
<220> FEATURE:
<221> NAME/KEY: MOD_RES
<222> LOCATION: (13)..(14)
<223> OTHER INFORMATION: Semi-conservative amino acid
<220> FEATURE:
<221> NAME/KEY: MOD_RES
<222> LOCATION: (16)..(16)
<223> OTHER INFORMATION: Semi-conservative amino acid
<220> FEATURE:
<221> NAME/KEY: MOD_RES
<222> LOCATION: (17)..(18)
<223> OTHER INFORMATION: Conservative amino acid

<400> SEQUENCE: 11

Cys Arg Ser Thr Val Xaa Xaa Ser Xaa Xaa Xaa Val Xaa Xaa Val Xaa
 1               5                  10                  15

Xaa Xaa Cys

<210> SEQ ID NO 12
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Ala or Val

<400> SEQUENCE: 12

Cys Arg Ser Thr Val Lys Val Ser Xaa Gln Gln Val Gln Gly Val His
 1               5                  10                  15

Ala Arg Cys

<210> SEQ ID NO 13
<211> LENGTH: 19
<212> TYPE: PRT
<213> ORGANISM: Sus sp.

<400> SEQUENCE: 13

Cys Arg Ser Thr Val Gln Ile Ser Ala Glu Lys Val Gln Asp Val Trp
 1               5                  10                  15

Val Arg Cys

<210> SEQ ID NO 14
<211> LENGTH: 19
<212> TYPE: PRT
<213> ORGANISM: Ovis sp.

<400> SEQUENCE: 14

Cys Arg Ser Thr Val Arg Met Ser Ala Glu Arg Val Gln Asp Val Trp
 1               5                  10                  15

Val Arg Cys

<210> SEQ ID NO 15
<211> LENGTH: 19
<212> TYPE: PRT
<213> ORGANISM: Rattus sp.

<400> SEQUENCE: 15

Cys Arg Ser Thr Val Gln Met Ser Lys Gly Gln Val Lys Asp Val Trp
 1               5                  10                  15

Ala His Cys

<210> SEQ ID NO 16
```

```
<211> LENGTH: 19
<212> TYPE: PRT
<213> ORGANISM: Mus sp.

<400> SEQUENCE: 16

Cys Arg Ser Thr Val Gln Met Ser Lys Gly Gln Val Lys Asp Val Trp
 1               5                  10                  15

Ala His Cys

<210> SEQ ID NO 17
<211> LENGTH: 19
<212> TYPE: PRT
<213> ORGANISM: Gallus sp.

<400> SEQUENCE: 17

Cys Lys Ser Val Val Glu Val Ser Ser Glu Gln Ile Val Asn Val Ile
 1               5                  10                  15

Val Arg Cys

<210> SEQ ID NO 18
<211> LENGTH: 19
<212> TYPE: PRT
<213> ORGANISM: Salmo sp.

<400> SEQUENCE: 18

Cys Thr Ala Arg Val Arg Val Thr Ala Glu Phe Thr Gln Val Val Ser
 1               5                  10                  15

Leu Asn Cys

<210> SEQ ID NO 19
<211> LENGTH: 19
<212> TYPE: PRT
<213> ORGANISM: Salmo sp.

<400> SEQUENCE: 19

Cys Thr Ala Arg Val Arg Val Thr Ala Glu Leu Thr Gln Val Val Ser
 1               5                  10                  15

Leu Asn Cys

<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      consensus polynucleotide
<220> FEATURE:
<221> NAME/KEY: modified_base
<222> LOCATION: (16)..(18)
<223> OTHER INFORMATION: a, c, g, t, unknown or other
<220> FEATURE:
<221> NAME/KEY: modified_base
<222> LOCATION: (25)..(33)
<223> OTHER INFORMATION: a, c, g, t, unknown or other
<220> FEATURE:
<221> NAME/KEY: modified_base
<222> LOCATION: (37)..(42)
<223> OTHER INFORMATION: a, c, g, t, unknown or other
<220> FEATURE:
<221> NAME/KEY: modified_base
<222> LOCATION: (46)..(48)
<223> OTHER INFORMATION: a, c, g, t, unknown or other

<400> SEQUENCE: 20
tgcagaagca ccgtgnnnyy ytctnnnnnn nnngtgnnnn nngtgnnntt tttttgc    57
```

```
<210> SEQ ID NO 21
<211> LENGTH: 57
<212> TYPE: DNA
<213> ORGANISM: Homo sapiens

<400> SEQUENCE: 21
tgcagaagca ccgtgaaggt atctgcccag caggtgcagg gcgtgcatgc tcgctgc      57

<210> SEQ ID NO 22
<211> LENGTH: 57
<212> TYPE: DNA
<213> ORGANISM: Sus sp.

<400> SEQUENCE: 22
tgcagaagca ccgtgcagat atctgctgag aaggtgcagg atgtgtgggt gcgttgt      57

<210> SEQ ID NO 23
<211> LENGTH: 57
<212> TYPE: DNA
<213> ORGANISM: Ovis sp.

<400> SEQUENCE: 23
tgcagaagca ccgtgcggat gtctgctgaa cgcgtgcagg acgtgtgggt tcgctgc      57

<210> SEQ ID NO 24
<211> LENGTH: 57
<212> TYPE: DNA
<213> ORGANISM: Rattus sp.

<400> SEQUENCE: 24
tgcaggagca cagtgcagat gtccaaggga caggtgaagg atgtgtgggc tcactgc      57

<210> SEQ ID NO 25
<211> LENGTH: 57
<212> TYPE: DNA
<213> ORGANISM: Mus sp.

<400> SEQUENCE: 25
tgcaggagca ctgtgcagat gtccaaggga caggtaaagg atgtgtgggc tcactgc      57

<210> SEQ ID NO 26
<211> LENGTH: 57
<212> TYPE: DNA
<213> ORGANISM: Gallus sp.

<400> SEQUENCE: 26
tgcaaaagcg ttgtagaagt ctccagtgag cagattgtga atgttattgt gcgatgc      57

<210> SEQ ID NO 27
<211> LENGTH: 57
<212> TYPE: DNA
<213> ORGANISM: Salmo sp.

<400> SEQUENCE: 27
tgcaccgcac gtgttcgcgt cactgcagag ttcactcagg ttgtgtccct gaactgt      57

<210> SEQ ID NO 28
<211> LENGTH: 57
<212> TYPE: DNA
<213> ORGANISM: Salmo sp.

<400> SEQUENCE: 28
tgcaccgcac gtgttcgtgt cactgcagag ctcactcagg ttgtgtccct gaactgt      57
```

```
<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Ser Glu Ala Asp Pro Ala Thr Cys Asp Phe Gln Arg
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Asn Ser Gln Ser Leu Ser Pro Tyr Leu Phe Arg
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Arg Gly Glu Pro Leu Tyr Glu Pro Ser Arg
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ser Tyr Leu Leu Gly Leu Thr Pro Asp Arg
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr His Val Pro Val Ala Val Cys Arg
 1               5                  10
```

SURGICAL APPLICATIONS FOR BMP BINDING PROTEIN

PRIORITY CLAIM

This application is a national stage application of PCT International Patent Application Number PCT/US2007/026315, filed Dec. 26, 2007, which claims priority to U.S. Provisional Patent Application No. 60/876,821, filed Dec. 22, 2006, and is a continuation-in-part of U.S. patent application Ser. No. 11/985,745, filed Nov. 16, 2007 now U.S. Pat. No. 8,193,312, which is a continuation-in-part of U.S. patent application Ser. No. 10/587,313, which has a 371 date of Apr. 28, 2008 now U.S. Pat. No. 8,188,219 and which is a national stage application of PCT/US05/02722, filed Jan. 28, 2005, which claims priority to U.S. Provisional Patent Application No. 60/539,903, filed Jan. 28, 2004.

The instant application contains a Sequence Listing which has been submitted in ASCII format via EFS-Web and is hereby incorporated by reference in its entirety. Said ASCII copy, created on Oct. 30, 2012, is named 38586375.txt and is 10,900 bytes in size.

BACKGROUND OF THE INVENTION

Growth factors are substances, including peptides, which affect the growth and differentiation of defined cell populations in vivo or in vitro. Normal bone formation occurs during development, bone remodeling occurs in adult life, and bone repair occurs in order to preserve the integrity of the skeleton. Bone formation, remodeling and repair involve bone resorption by osteoclasts and bone formation by osteoblasts. Cell differentiation and the activity of osteoblasts and osteoclasts are regulated by growth factors. Thus, any interference between the balance in cell differentiation and resorption can affect bone homeostasis, bone formation and repair.

Osteoblasts are derived from a pool of marrow stromal cells (also known as mesenchymal stem cells). MSC are present in a variety of tissues and are prevalent in bone marrow stroma. MSC are pluripotent and can differentiate into chondrogenic or osteogenic cells including osteoblasts, chondrocytes, fibroblasts, myocytes, and adipocytes.

The induction of ectopic bone formation by demineralized bone matrix (DBM) has been described. (Urist, M. R.: Bone: Formation by autoinduction. *Science* 150:893-899, 1965; Urist, et al., Purification of bovine morphogenetic protein by hydroxyapatite chromatography. *Proc. Natl. Acad. Sci. USA* 81:371-375, 1984; Urist, M. R. Emerging concepts of bone morphogenetic protein. In *Fundamentals of Bone Growth: Methodology and Applications*, Boston C.R.C. Press, pp. 189-198, 1991.) Further, the properties of the partially purified protein fraction, bone morphogenic protein/non-collagenous protein ("BMP/NCP" or "BMP"s) have been described. (Urist, et al. Methods of Preparation and Bioassay of Bone Morphogenetic Protein and Polypeptide Fragments. In *Methods in Enzymology*. Vol. 146. New York, Academic Press, pp. 294-312, 1987; Urist, et al., Hydroxyapatite affinity, electroelution, and radioimmunoassay for identification of human and bovine bone morphogenetic proteins and polypeptides. In *Development and Diseases of Cartilage and Bone Matrix*. New York, Alan R, Liss, Inc., pp. 149-176, 1987.)

BMP/NCP was never purified to homogeneity, but other investigators have used similar starting materials to clone a number of recombinant "BMPs." However several of these molecules have little or no osteogenic activity. "BMPs" and other osteogenic factors have been studied for use in clinical applications. However, the cost of using minimally effective dosages of BMP-7 (also known as OP-1), for example has been a limiting factor in clinical use. Therefore, effective and affordable compositions and methods are desired for clinical applications relating to bone.

Adjuvant therapeutics to enhance bone healing are important in many aspects of orthopedics, but are especially important for spinal fusion where prompt and thorough osteogenesis is critical. The most useful agents currently available include bone growth factors, such as bone morphogenetic proteins (BMPs). These proteins induce the recapitulation of endochondral bone formation among undifferentiated mesodermal cells. However, their usefulness is limited by expense and by local adverse effects such as unwanted ectopic bone formation and inflammatory responses associated with doses currently used for spinal fusion procedures.

Furthermore, potential systemic adverse effects of high dose BMPs when to be used for longer fusions has not been fully determined. Therefore, a number of strategies are being developed to provide safer, less expensive and more efficacious adjuvant agents.

The use of BMP-2 as a bone generator for spinal fusion is gaining increased popularity. Recent studies have shown that it may be used effectively for both anterior and posterior fusion procedures through the whole spinal column. However, its high expense as well as the reported local side effects such as unwanted bone formation and dangerous swelling at the neck after the anterior cervical fusion procedure has prevented its extensive use for spinal procedures. Focus has now shifted to increase the effectiveness of BMP-2 while decreasing its dose and controlling the side effects. The main limitation is the need for better delivery systems that provide a sustained, biologically appropriate concentration of BMP-2 at the side of fusion bed. Delivery needs to be sustained, because BMPs have exceedingly short biological half-lives, usually the order of minutes or hours, rather than the days or weeks needed to stimulate a complete osteogenic response. For example, rBMP-2 has been described as having a half-life of only a few hours.

BRIEF SUMMARY OF INVENTION

The inventions are related to a cyclic peptide designated BMP Binding Peptide (BBP) that avidly binds growth factors, such as rhBMP-2. BBP increases the rate and degree to which rhBMP-2 induces bone formation. BBP may accomplish this by increasing the residency rates of other bone growth factors. However, BBP alone induces calcification of chondrogenic, osteogenic and osteoblastic cells. Compositions and substrates including BBP, antibodies to BBP and methods of using BBP are useful in applications relating to bone.

In one embodiment, the invention may include a method of treatment with agents for maintaining bone homeostasis, enhancing bone formation and/or enhancing bone repair.

In one embodiment, the invention includes methods and devices for increasing the residency times of bone inducing substances, such as BMP. In one embodiment, the invention includes methods and devices for increasing the rate and overall osteogenic activity of bone inducing substances, such as BMP. Further, in one embodiment, the invention includes methods and devices for reducing time required for the effect of osteogenesis and calcification of bone inducing substances.

In one application of the invention, the method may be applied to induce the local repair of bone or to treat bone related disorders, such as osteoporosis. In one embodiment of the invention, BBP may be used to induce the effects of other bone growth factors on bone fusion in membraneous bone (such as spinal fusion) or in endochondral bone.

In one embodiment, the invention may include implants having agents or seeded with pluripotential or differentiated cells for inducing bone formation or repair. The invention may also include the application of substances or differentiated cells at a site where bone formation or bone repair is desired.

This invention is advantageous at least in that BBP alone or in combination with other growth factors enhances calcification of chondrogenic or osteogenic precursor cells. Further, this invention is advantageous at least in that BBP enhances osteogenesis to occur faster to a greater extent, which may improve the clinical rate and effectiveness of treatment with BMP, and reduce doses and therefore the costs and side effects of BMP treatment alone.

These, as well as other objects, features and benefits will now become clear from a review of the following detailed description of illustrative embodiments and the accompanying drawings.

BRIEF DESCRIPTION OF DRAWINGS

FIG. 1A are BBP bovine (1) amino acid and (2) nucleic acid sequences, respectively; FIG. 1B is a partial amino acid sequence of the bovine BMP binding protein ("BBP") showing the cystatin homology region, the BMP-2 homology region, and the TGF-β receptor II homology domain.

FIG. 2 is an amino acid sequence alignment of human BMP-2 and the BMP-2 homology region in bovine SPP-24; (i, identical; c, conservative substitution; sc, semi-conservative substitution).

FIG. 3 is an amino acid sequence alignment of bovine fetuin and human TGF-β receptor II (above) and of human TGF-β receptor II and the TGF-β receptor II homology domain of bovine SPP-24 (corresponding to BBP) (bottom); (i, identical; c, conservative substitution; sc, semi-conservative substitution).

FIG. 4 is a radiogram of mouse hind quarters 21 days after implantation of 500 μg of BBP in atelocollagen (top) or atelocollagen alone (bottom).

FIG. 5 is a histological section of mouse muscle 21 days after implantation of 500 μg of BBP in atelocollagen. (H & E stain. Original magnification 100×.)

FIG. 6 are radiograms of mouse hind quarters 21 days after implantation of 5 μg of rhBMP-2 (left) or 5 μg of rhBMP-2 plus 500 mg of BBP (right).

FIG. 10 is a bar graph depicting the percentage of rhBMP-2 retention over 1, 3 and 7 days in the presence or absence of BBP.

FIG. 11 includes amino acid sequences against which specific SSP-24/BBP antibodies have been generated.

FIG. 14 A is a chart showing the amino acid sequences for BPP in various species (SEQ ID NOS 11, 1 and 12-19, respectively, in order of appearance). FIG. 14 B is a list of the nucleic acid sequences for BPP in various species (SEQ ID NOS 20-28, respectively, in order of appearance).

DETAILED DESCRIPTION OF ILLUSTRATIVE EMBODIMENTS

Figure 7:
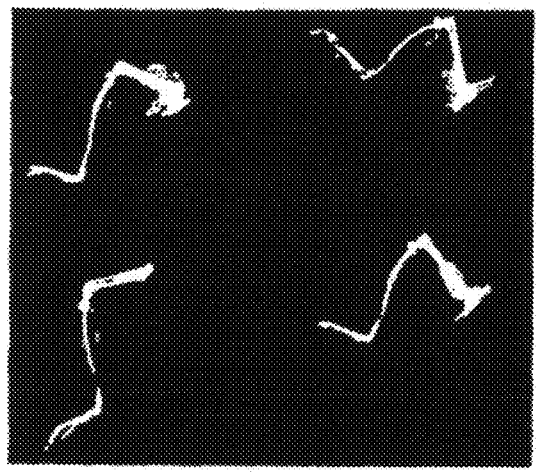
FIG. 7 are radiograms of mouse hind quarters 9 (top) and 12 (bottom) days after implantation of 5 μg of rhBMP-2 (left) or 5 μg of rhBMP-2 plus 500 mg of BBP (right).

One embodiment of the invention comprises a peptide having the amino acid sequence of SEQ ID NO: 1. The bovine derived amino acid SEQ ID NO: 1 has been designated BBP, and SEQ ID NO: 2 corresponds to the bovine nucleic acid sequence encoding BBP.

One embodiment of the invention comprises a peptide having the amino acid sequence of SEQ ID NO: 12, which is the sequence of human BBP. SEQ ID NO: 21 corresponds to the human nucleic acid sequence encoding human BBP.

BBP is a 19 amino acid, 2.1 kD peptide, derived from a 18.5 kD fragment of a known 24 kD secreted phosphoprotein ("SPP-24"). SPP-24 is illustrated by SEQ ID NO: 2. Notably, SPP-24 inhibits BMP-2 induced bone formation. BBP contains the cystatin-like domain of SPP-24. BBP is expressed at least in the liver and bone (including at least demineralized cortical bone and periosteum).

The BBP amino acid sequence is similar to the TGF-β/BMP-binding region of fetuin, a member of the cystatin family of protease inhibitors. BBP avidly binds rhBMP-2 (recombinant human BMP-2) with a $K_D$ of $\times 10^{-5}$ M. BBP may also bind other molecules having similar binding domains to BMP-2, such as other TGF-β proteins (including but not limited to BMP-4, BMP-7 (OP-1), BMP-6, BMP-8 (OP-2), BMP-9 and TGF-β) and affect their retention rates and/or activity as well. There is a high degree of sequence similarity (about 90%) between BMP-4 and BMP-2, for example. Additionally, the various ostroinductive BMPs (BMP-2, BMP-4, BMP-6, BMP-7 and BMP-9) have been demonstrated to bind to the same receptors (with some variation in affinities). Therefore, given the sequence and binding similarities, binding with these additional BMPs is expected. Additional growth factors useful in this invention may include: GDF5, and other BMPs such as, BMP-3, BMP-4, BMP-5, BMP-6, BMP-7, BMP-8, BMP-9.

BBP alone induces calcification of vertebrate chondrogenic and osteogenic precursor cells. BBP increases the increases the rate and degree to which rhBMP-2 induces bone formation. Surprisingly, BBP combined with BMP-2 in vivo causes osteogenesis to occur faster and to a greater extent and with smaller amounts of rhBMP-2, than compared with the effect of BMP-2 alone. This result was unexpected given the role of SSP-2 which inhibits bone formation by BMP-2, as discussed above.

For example, when implanted alone in mouse muscle, the BBP induces dystrophic calcification. The process of bone formation in repair or ectopic bone formation the "mouse hindquarter" or "muscle pouch" model recapitulates endochondral bone formation. The first step involves the production of cartilage, which is replaced by bone. This same process that occurs during endochondral bone formation in development, while some membraneous bone formation occurs directly without a cartilage intermediary.

In one embodiment of the invention, a peptide comprising a fragment of BBP may be useful, if the fragment similarly increases degree or rate of osteogenesis by BMP-2 in mammalian cells, or increases degree or rate of calcification in vertebrate cells, or specifically mammalian chondrogenic or osteogenic progenitor cells.

Forms of BBP having modifications of the amino acid SEQ ID NO: 1 may also be useful in this invention. For example, the conserved amino acid sequences of BBP between species, deletional or insertional modifications, conservative or semi-conservative substitutional modifications are intended to be encompassed in the claimed BBP, to the extent that the modified amino acid sequences increase the residency time and or activity of BMP-2 or other TGF-β homologous molecules. BBP is a β-pleated sheet-turn-sheet pleated sheet molecular motif ("B-T-B"). It is currently believed that growth factor binding amino acids reside in the T-section. Therefore, amino acid substitutions in the T-section may affect activity of BBP to a greater extent than substitutions in the B regions.

As above, BPP is believed to increase the effect of growth factors, like BMP-2 by increasing the amount of time ("residency time") that a growth factor remains at the site of implantation, and/or the overall activity of BMP-2 or other TGF-β homologous molecules. BMP alone, for example, is rapidly removed from implantation sites, while implantation of BMP with BBP has been shown to increase residence time. The increase in residency time may be attributed to, for example: 1) BPP's ability to increase the half-life of growth factors (such as by reducing the rate of proteolysis), and/or 2) decrease the diffusion rate of growth factors from an application site.

One embodiment of the invention comprises a peptide having the sequence of SEQ ID NO: 11: C-R-S-T-V-X-Z-S-X-X-X-V-X-X-V X-Z-Z-C, which is the mammalian consensus sequence for BBP. FIG. 14A shows the homology in amino acid sequence across bovine (SEQ ID NO: 1; nucleic acid sequence set forth at SEQ ID NO: 2), human (SEQ ID NO: 12; nucleic acid sequence set forth at SEQ ID NO: 21 (position 9 is either A or V), porcine (SEQ ID NO: 13; nucleic acid sequence set forth at SEQ ID NO: 22), ovine (SEQ ID NO: 14; nucleic acid sequence set forth at SEQ ID NO: 23), rat (SEQ ID NO: 15; nucleic acid sequence set forth at SEQ ID NO: 24), and mouse (SEQ ID NO: 16; nucleic acid sequence set forth at SEQ ID NO: 25) BBP. FIG. 14A also shows highly conserved regions in chicken (SEQ ID NO: 17; nucleic acid sequence set forth at SEQ ID NO: 26), salmon (SEQ ID NO: 18; nucleic acid sequence set forth at SEQ ID NO: 27) and trout (SEQ ID NO: 19; nucleic acid sequence set forth at SEQ ID NO: 28).

In FIG. 14 A, "X" and "Z" are used to denote amino acid substitutions that are understood to be semi-conservative or conservative, respectively. Conservative substitutions include amino acids selected from the same group, and semi-conservative substitutions include substitutions that are not believed to affect the BMP-2 binding domain or the function of the BBP. For example, the substitution at position 6 is conservative between human, rat and ovine, but semi-conservative with some other species because the amino acids reported at that position in different species are: Q and E (Q in porcine, rat, and mouse BBP, and E in chicken). Although K and R are both classified as basic amino acids, Q is classified as an uncharged polar amino acid, therefore the substitution is not conservative. The substitution is semi-conservative, however, because the function of BBP is believed to be unaffected. Semi-conservative substitutions are also found at positions 9, 10, 11, and 16. At position 9, the amino acids A is found in bovine, human, porcine and ovine BBP, compared to K in rat and mouse BBP. At position 10, the amino acid E is reported for bovine, porcine, and ovine BBP, human BBP contains Q at that position, and rat and mouse BBP contain the amino acid G. At position 11, the amino acid Q is found in bovine, human, rat and mouse, whereas K, is reported for porcine BBP and R for ovine BBP. At position 16, W is found in bovine, porcine, ovine, rat and mouse BBP, whereas human BBP contains an H. There are also semi-conservative substitutions at positions 13 and 14 between rat/human, as opposed to other species.

An example of a conservative substation is found at position 7. At this position, different hydrophobic amino acids are observed in different species, namely, M in bovine, ovine, rat, and mouse BBP, compared to V in human and I in porcine BBP. This substitution is considered conservative because M, V, and I are all hydrophobic amino acids. Other conservative substitutions occur at positions 17 and 18. Two hydrophobic amino acids, A and V, are found at position 17. At position 18, two basic amino acids, R and H, are found.

One embodiment of the invention may be a composition including BBP which increases degree or rate of calcification in vertebrate cells, or more specifically mammalian chondrogenic or osteogenic precursor cells. Further, the invention may be including BBP which increases degree or rate of osteogenesis by BMP-2, and one of BMP-2 or demineralized bone matrix. Further, the composition may additionally or alternatively include other TGF-β family members, including but not limited to BMP-4 or BMP-7 separately or mixtures thereof.

In one embodiment, the invention may include a medicament for use in inducing the rate or degree of osteogenesis in a vertebrate including a therapeutically effective dosage of BBP alone or in combination with a growth factor, such as BMP or DBM. The invention may further include, a medicament for use in inducing the rate or degree of calcification in a vertebrate including a peptide comprising BBP.

In one embodiment, BBP or the combination of BPP and one or more other growth factors may be placed on or in a substrate or carrier, such as a collagen sponge or orthopedic implant or prosthesis, for implantation at a site where bone formation and/or implant integration is desired.

Applications for BBP. A number of applications for BBP are suggested from its pharmacological (biological activity) properties. For example, BBP alone or in combination with other TGF-family members such as BMP-2, BMP-4 and BMP-7, or demineralized bone matrix may be used in clinical or research methods for inducing bone formation, maintaining bone homeostasis and/or enhancing bone repair. BBP may be used alone or in combination to treat developmental or homeostatic bone disorders (such as osteoporosis), bone injury (such as fracture healing flat (e.g., membranous) and long (e.g., endochondral) bones, non-union fractures and reconstructive surgery. The invention may also be used in treating periodontitis, periodontal regeneration, alveolar ridge augmentation for tooth implant reconstruction, treatment of non-union fractures, sites of knee/hip/joint repair or replacement surgery.

By way of example, BMP has been demonstrated to be effective in providing spinal fusion, but has limitations to widespread use due to adverse side effects, such as causing inflammation and ectopic bone formation, particularly in the cervical spine. In one embodiment BBP may be used in conjunction with lower doses of BMP to preserve its efficacy, an increase its retention at the application site. As discussed herein, BBP has been demonstrated to bind BMP, including recombinant human BMP-2 enabling a two fold retention of rhBMP-2 for up to seven days in vitro and in vivo.

Clinical indices of a method or compounds ability to maintain bone homeostasis is evidenced by improvements in bone density at different sites through out the body as assessed, at least by DEXA scanning. Enhanced bone formation in a healing fracture is routinely assessed by regular X-ray of the fracture site at selected time intervals. More advanced techniques for determining the above indices, such as quantitative CT scanning or quantitative histological methods (e.g., tissue is processed, stained, and microscopically examined and bone defined an measured with image analysis) may be used. Further, measures of bone density, bone area, bone mineral content, formation of ectopic bone, and increases in the opacity of tissue upon X-ray examination, expression of alkaline phosphatase activity, calcium incorporation, mineralization or expression of osteocalcin mRNA may be used to observe the effects of BBP calcification and/or osteogenesis The invention may also include the use of agents which inhibit osteoclastic bone resorption. Agents which may be useful in this invention to effect osteoclastic bone resorption include, but are not limited to, bisphosphonates, the selective estrogen receptor modulators, calcitonin, and vitamin D/calcium supplementation. The invention may also include the use of agents which induce osteoblastic bone formation. Agents which may be useful in this invention include, but are not limited to PTH, sodium fluoride and growth factors, such as insulin-like growth factors I and II.

The in vivo models used to show the calcification effects of BBP alone or osteogenic effects in combination with BMP have been used previously in demonstrating similar behaviors of other compounds. In particular, in vivo models have also previously been able to successfully predict the in vivo osteogenic effects of compounds such as BMP and insulin like growth factors (IGF). Specifically, it has been demonstrated that the osteogenic effects of BBP in an animal model using rat femur, ectopic bone formation model. Therefore it is anticipated that, based on these similar findings, BBP will have osteogenic effects in vivo in humans. Demonstration of osteogenic effects of a compound in these in vivo models are necessary prior to trials that would demonstrate their effects in vivo humans.

Therapeutically effective dose. A therapeutically effective dose of BBP or a TGF-β family member useful in this invention is one which has a positive clinical effect on a patient or desired effect in cells as measured by the ability of the agent to enhance calcification or osteogenesis, as described above. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

This invention is advantageous and unexpected us in at least the dosage of BMP-2 required to induce a given rate or degree of osteogenesis may be reduced when BMP-2 is combined with BBP. This is advantageous at least in reducing the cost of treatment, as BMP can be costly for some applications. Further, reducing treatment levels of BMP (or other bone growth factors) by treating in combination with BMP may also reduce side effects which are related to the amount of BMP used, including for example, inflammation within the soft tissue of the neck or ectopic bone formation. Thus, the use of BBP as a bone growth factor binding agent to increase exogenous growth factor retention, can aid in overcoming negative aspects of growth factor use by reducing the amount of growth factor needed to achieve healing.

Dosage Form. The therapeutically effective dose of an agent included in the dosage form may be selected by considering the type of agent selected and the route of administration. The dosage form may include a agent in combination with other inert ingredients, including adjutants and pharmaceutically acceptable carriers for the facilitation of dosage to the patient, as is known to those skilled in the pharmaceutical arts.

Therapeutic formulations of BBP (when claimed is intended to include modifications or fragments thereof), may be prepared for storage by mixing the BBP having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; anti-oxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or poly(ethylene glycol) (PEG).

The dosage form may be provided in preparations for subcutaneous (such as in a slow-release capsule), intravenous, intraparitoneal, intramuscular, peri- or intraskeletal for example. Any one or a combination of agents may be included in a dosage form. Alternatively, a combination of agents may be administered to a patient in separate dosage forms. A combination of agents may be administered concurrent in time such that the patient is exposed to at least two agents for treatment.

Additional Agents. The invention may include treatment with an additional agent which acts independently or synergistically with BBP to enhance calcification osteogenesis. For example, BBP may be combined with BMP, bisphosphonates, hormone therapy treatments, such as estrogen receptor modulators, calcitonin, and vitamin D/calcium supplementation, PTH (such as Forteo or teriparatide, Eli Lilly), sodium fluoride and growth factors that have a positive effect on bone, such as insulin-like growth factors I and II and TGF-β. Those skilled in the art would be able to determine the accepted dosages for each of the therapies using standard therapeutic dosage parameters, or reduced dosages where the effects of BBP are synergistic with the secondary agent, such as BMPs.

BBP is currently thought to act upon BMP-2 at least by increasing its residency time with a substrate. One embodiment of the invention is a method of detecting the ability of BBP to enhance the residency time of a TGF-β homologous molecule including applying an amount of the TGF-β homologous molecule at a first and second selected location. Further, applying a selected amount of BBP at the first selected location, and finally detecting the amount of the TGF-β homologous molecule at the first and second location after a selected time period; and calculating the difference between the amount of the TGF-β homologous molecule at the first and second location.

In one embodiment, the invention may include a method of enhancing the rate or degree of osteogenesis in vertebrate tissue including application of BBP which increases degree or rate of osteogenesis by BMP-2 in mammalian cells and one of a TGF-β family member, such as BMP-2 or demineralized bone matrix.

In one embodiment, the invention may include a method of inducing calcification of vertebrate tissue, or more specifically vertebrate chondrogenic or osteogenic precursor cells, including application of BBP.

In one embodiment, the invention may include a method of enhancing the rate or degree of osteogenesis in vertebrate tissue including administering chondrogenic or osteogenic precursor cells to the patient at a location proximate to the desired location of osteogenesis; further, administering BBP, and administering one of a TGF-β family member, such as BMP-2 or demineralized bone matrix.

In one embodiment, the invention may include a method of enhancing the rate or degree of calcification in vertebrate tissue including administering osteogenic cells to the patient at a location proximate to the desired location of calcification and further, administering BBP.

In one embodiment, the invention may include method of enhancing the rate or degree of osteogenesis in a vertebrate including treating vertebrate undifferentiated mesynchymal stem cells with one of a TGF-β family member, such as BMP-2 or demineralized bone matrix to induce osteogenesis of the cells. Further, treating the vertebrate mesynchymal stem cells with BBP; and administering the vertebrate mesynchymal stem cells to the patient at a location proximate to the desired location of osteogenesis.

For example, mammalian cells, such as mesenchymal stem cells can be harvested, from the patient or a cell donor. The cells may be injected in a location where bone formation or repair is desired (such as a fracture site or implant site where bone growth is needed), or first treated with BBP and/or BMP. The cells may then be re-administered to the patient, either systemically or at a selected site at which osteogenesis of calcification is desired. Additionally, the patient may by treated locally or systemically with at least one additional agent which effects osteogenesis or calcification.

Figure 12B:
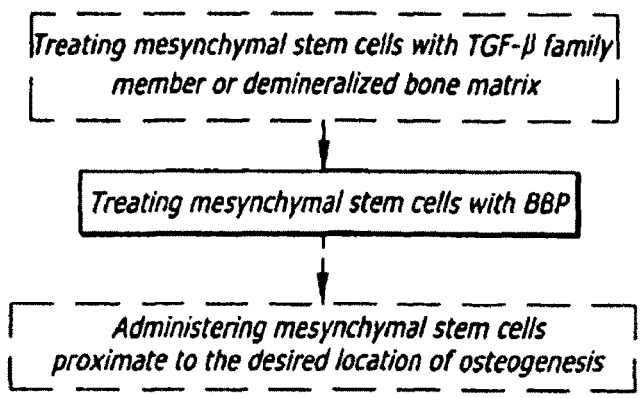
FIGS. 12 A & B depict flowcharts of exemplary methods of the invention.

FIGS. 12A and B depict flowcharts of exemplary methods of the invention, the steps of which may be performed in any order.

One embodiment of the invention may include an article of manufacture comprising BBP immobilized on a solid support. The solid support may further include a TGF-β family member, such as BMP-2 or demineralized bone matrix.

One embodiment of the invention may include an implant for use in vivo including, a substrate where at least the surface of the implant includes BBP. The implant may further include MSC, chondrocytic or osteoblastic progenitor cells. Further, the implant may be formed into the shape of a pin, screw, plate, or prosthetic joint, for example.

Figure 13A:
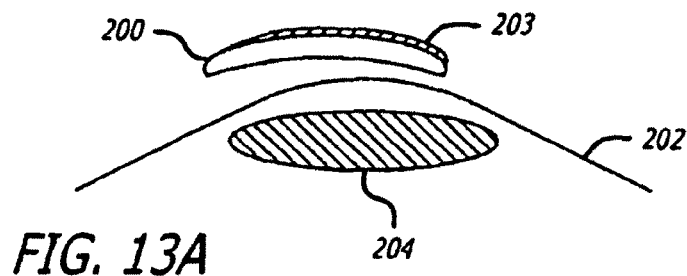
FIGS. 13 A & B are schematic depictions of two embodiments of the invention.

For example, FIGS. 13A & B depict two embodiments of the present invention. In FIG. 13A, the invention may include implants or grafts (200) for use in the body comprising, a substrate having a surface (201), wherein at least the surface of the implant includes BBP (203) in an amount sufficient to induce, calcification or osteogenesis in the surrounding tissue. The implant may include mesynchymal stem cell, chondrogenic or osteogenic cells expressing BBP, and/or BMP-2, demineralized bone matrix, or collagen cultures. The implant may be in the form of, but are not limited to pins, screws, plates or prosthetic joints which may be placed in the proximity of or in contact with a bone (202) that are used to immobilize a fracture, enhance bone formation, or stabilize a prosthetic implant by stimulating formation or repair of a site of bone removal, fracture or other bone injury (204).

Figure 13B:
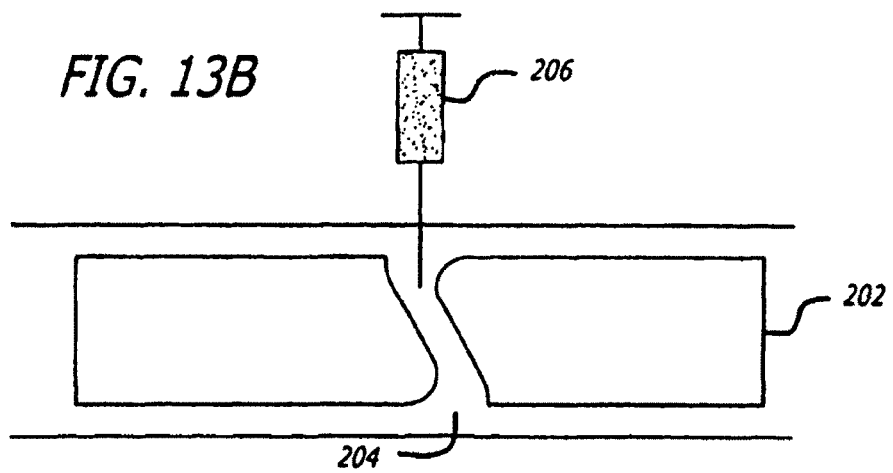

As shown in FIG. 13B, the invention may also include the in vitro (such as on cultures of collagen or chondrocytes) or in vivo application of at a least BBP containing composition or BBP expressing cells (206) in the proximity of or in contact with a bone (202), an implant (200) at a site of bone removal, fracture or other bone injury (204) where osteogenesis and/or calcification is desired. The BBP composition may be applied in combination with other agents such as BMP-2, demineralized bone matrix, or collagen cultures.

For example, the use of stem cells for treating bone related disorders in humans has also been examined. Infusion of osteoblastic progenitor stem cells from a healthy individual into a diseased individual has been shown to improve bone density in these patients. Cells may be pretreated with BMP and BPP, or applied concurrently therewith.

In one embodiment, the invention may include a monoclonal or polyclonal antibody having selective binding to any portion of BBP, or the BBP portion of the BBP precursor, SSP-24.

BBP or fragments thereof may be fused (for example by recombinant expression or in vitro covalent methods) to an immunogenic polypeptide and this, in turn, may be used to immunize an animal in order to raise antibodies against BBP. Antibodies are recoverable from the serum of immunized animals. Alternatively, monoclonal antibodies may be prepared from cells from the immunized animal in conventional fashion. Immobilized antibodies may be useful particularly in the detection or purification of BBP.

Two examples of specific peptide sequences against which rabbit polyclonal antibodies have been generated include: (1) An antibody against the peptide sequence "IQETTCRRE-SEADPATCDFQRGYHVPVAVCRSTVRMSAEQV" (FIG. 11 SEQ ID NO: 3) that reacts with both bovine and human SSP-24, the BBP precursor. This antibody was generated in rabbits immunized with the synthetic peptide indicated above. Further, (2) An antibody directed against the sequence "CGEPLYEPSREMRRN" (FIG. 11 SEQ ID NO: 4) that was also produced in rabbits immunized with a synthetic peptide corresponding to the indicated sequence. This second antibody reacts with bovine SSP-24. The N-terminal cysteine is not a part of the native SSP-24 sequence; but is preferably included to allow the peptide to be conjugated to chromatographic resins for affinity chromatography. Additional peptide sequences may be identified for specific binding to BBP, and sequences may be selected so as to create an antibody having selective binding with BBP, but so as to not interfere with BBP binding, such as the region of BBP which binds with BMP-2 (including SEQ ID NOS 3 and 4) or other TGF-β family members. These specific peptide sequences can be used to generate monoclonal antibodies, which preparation methods are known in the art.

Antibodies against the sequences above, corresponding sequences in the mouse, human, and rat genome, or any derivatives of the immunogenic sequences are also useful in this invention. These antibodies are useful in at least to the extent that they recognize the BBP amino acid sequence with high specificity. Such antibodies may also be useful in inhibiting protein specific interactions of BBP with other molecules where the antibody binds to a location on the peptide which interacts with other molecules. The inhibition of BBP activity in situations where the rate or degree of chondogenesis or osteogenesis may be modified.

In one embodiment the invention, antibodies specific for BBP may be useful in decreasing the degree or rate of osteogenesis by BMP-2 in vertebrate cells or decreasing degree or rate of calcification in vertebrate cells, or more specifically in mammalian chondrogenic or osteoblastic precursor cells.

One embodiment of the invention may also include a method of using BBP selective antibodies to detect the presence of SSP-24/BBP in sample (including but not limited to a cell culture, tissue sample, peptide fraction, Western blot) including exposing the sample to the BBP selective antibody and visualizing the complex of SSP-24/BBP and BBP antibody.

In one embodiment of the invention, BBP antibodies may be used for the affinity purification of the BBP from recombinant cell culture or natural sources. BBP antibodies that do not detectably cross-react with other growth factors can be used to purify BBP from these other family members.

In one embodiment, the invention may include a nucleic acid construct comprising a DNA or RNA nucleic acid sequence encoding BBP, or modified sequences corresponding to the modified amino sequences described above.

The invention may also include, an expression vector operatively linked to a nucleic acid sequence encoding BBP, or precursor SSP-24 Further, a transformant may be obtained by introducing the nucleic acid construct encoding for BBP, or its precursor SSP-24 into a host cell.

Practice of this invention may include the use of an oligonucleotide construct comprising a sequence coding for BBP and for a promoter sequence operatively linked in a mammalian or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. Such cloning vectors are well known to those of skill in the art. Expression vectors, unlike cloning vectors, may contain an inducible or constitutive promoter which is recognized by the host organism and is operably linked to the BBP nucleic acid. The nucleic acid may be operably linked when it is placed into a functional relationship with another nucleic acid sequence. For example, DNA for a pre-sequence or secretory leader is operably linked to DNA for a polypeptide if it is expressed as a pre-protein which participates in the secretion of the polypeptide.

One embodiment of the invention may also include a method of using DNA or RNA nucleic acid sequences complimentary and having specific binding for the DNA or RNA sequences encoding BBP to detect the presence of BBP DNA or RNA in a sample, respectively (including but not limited to a cell culture, tissue sample, nucleic acid fraction, or Southern or Northern blot) including exposing the sample to the complimentary BBP DNA or RNA sequences and visualizing the complex of hybrids.

Example 1

Extraction and Separation of Non-Collagenous Bone Proteins (NPCs)

Methods: NCPs were extracted from defatted, demineralized human cortical bone powder with 4 M GuHCl, 0.5 M CaCl$_2$, 2 mM N-ethylmalemide, 0.1 mM benzamidine HCl, and 2 mM NaN$_3$ for 18 hr at 6° C. Residual collagen and citrate-soluble NCPs were extracted by dialysis against 250 mM citrate, pH 3.1 for 24 hours at 6° C. The residue was pelleted by centrifugation (10,000×g at 6° C. for 30 min), defatted with 1:1 (v/v) chloroform: methanol for 24 hr at 23° C., collected by filtration and dried at 22° C. The material was resuspended in 4 M GuHCl, dialyzed against 4 M GuHCl, 0.2% (v/v) Triton X-100, 100 mM Tris-HCl, pH 7.2 for 24 hr at 6° C., then dialyzed against water, and centrifuged at 10,000×g for 30 min at 6° C. The pellet was lyophilized and subsequently separated by hydroxyapatite chromatorgraphy.

Chromatography was conducted using a BioLogic chromatography workstation with a CHT-10 ceramic hydroxyapatite column (BioRad, Hercules, Calif.). Bovine BMP/NCP was solublized in 6 M urea, 10 mM sodium phosphate, pH 7.4. The sample was loaded onto the hydroxyapatite column and the unbound fraction was collected. Bound proteins were eluted with increasing concentration of sodium phosphate to 300 mM over a linear gradient of five column volumes. Five ml fractions were collected during the course of the run. The fraction which separated at 180 mM phosphate was separated further by SDS-PAGE electrophoresis. A band corresponding to a $M_r$ of 18.5 was excised and submitted for sequence analysis by matrix assisted laser-desorption ionization/time of flight mass spectroscopy (MALDI/TOF MS).

Results: Sequence Identification and Analysis: The fraction of bBMP/NCP which eluted from hydroxyapatite at 180 mM phosphate was separated by SDS-PAGE electrophoresis and the material with a $M_r$ of 18.5 kD was submitted for MALDI/TOF MS analysis. The major protein component of this material was determined to be a fragment of SPP-24 on the basis of six peptides with sequences identical to regions of that protein. (Hu, et al., Isolation and molecular cloning of a novel bone phosphoprotein related in sequence to the cystatin family of thiol protease inhibitors. J. Biol. Chem. 270:431-436, 1995.) The sequences of these peptides are shown in Table 1.

TABLE 1

Identification of the 18.5 kD protein by MALDI/TOF mass spectroscopy and peptide fingerprinting.

| Expected Mass$^a$ | Observed Mass$^a$ | Peptide Sequence | SEQ ID NO: |
|---|---|---|---|
| 1526.574 | 1526.53 | ESEADPATCDFQR* | 29 |
| 1411.600 | 1411.71 | VNSQSLSPYLFR | 30 |
| 1291.406 | 1291.41 | SRGEPLYEPSR | 31 |
| 1249.409 | 1249.48 | NSYLLGLTPDR | 32 |
| 1158.363 | 1158.27 | GYHVPVAVCR* | 33 |

*modified cystein; a = peptide masses are expressed as [M + H$^+$]

Analysis of this sequence with the SWISS-PROT data base revealed the cystatin-like domain which had been previously described, but no other sequence similarities of relevance to bone metabolism. (Hu, et al.) However, it is known from other work that other cystatin-like proteins interact with proteins having a role in bone metabolism. Specially, members of the cystatin family have TGF-β and BMP-2 binding properties based on similarities to the TGF-β receptor. (Brown, et al., Friends and relations of the cystatin superfamily-new members and their evolution: Protein Sci. 6:5-12, 1997; Demetriou, et al., Fetuin/α2-HS glycoprotein is a transforming growth factor-β type II receptor mimic and cytokine antagonist. J. Biol. Chem. 271:12755-12761, 1996.) However, fetuin antagonizes BMP activity. (Hu, et al.) Therefore, a manual comparison was made of the cystatin-like region of SPP-24 and the cystatin-like domain of fetuin.

FIG. 1B is a partial amino acid sequence of the bovine SSP-24, the BMP-2 homology region, and the TGF-β receptor II homology domain. Underlined amino acids have been confirmed to be present by mass spectroscopy. (GenBank Accession Number U08018; Hu, et al.)

Two regions of interest were identified in the cystatin-like region of SPP-24. One region had some sequence similarity to BMP-2, whereas the other region had sequence similarity to the TGF-β receptor II homology domain of fetuin. That part of the sequence of SPP-24 which contains these two regions is shown in FIG. 1B.

Comparisons of the two regions of interest to human BMP-2 and human TGF-β receptor II are shown in FIGS. 2 and 3. FIG. 2 is an amino acid sequence alignment of human BMP-2 and the BMP-2 homology region in bovine SPP-24. FIG. 3 is an amino acid sequence alignment of bovine fetuin and human TGF-β receptor II (top) and of human TGF-β receptor II and the TGF-β receptor II homology domain of bovine SPP-24 (corresponding to BBP)(bottom). Alignment of the SPP-24, fetuin, human BMP-2, and human TGF-β receptor II sequences was accomplished using the T-Coffee program. (Notredame, et al, T-Coffee: A novel method for multiple sequence alignments. *J. Molecular Biol.* 302:205-217, 2000.) Synthetic peptides corresponding to these two regions were obtained and subjected to chemical and in vivo analysis as described below.

Example 2

In Vivo Activity of BBP

Methods: The osteogenic activity of material was tested using male Swiss-Weber mice aged 8 to 10 weeks were used (Taconic Farms, Germantown, N.Y.). Prior to the assay, the BBP was solubilized and lyophilized into 2 mg of atelocollagen. The dried material was placed in a #5 gelatin capsule and sterilized by exposure to chloroform vapor. To conduct the assay, mice were anesthetized using 1% isoflurane delivered in oxygen at 2 l/min through a small animal anesthesia machine (VetEquip, Pleasanton, Calif.). Animals were affixed to a surgery board and the fur over the hindquarters shaved. The skin was cleaned with 70% ethanol and a midline incision made over the spine adjacent to the hindquarters. Blunt dissection with scissors was used to expose the quadriceps muscle on one side. A small pouch was made in the muscle using the point of scissors and the #5 capsule containing the test material was inserted into the pouch. The skin was then closed with three 11 mm Michel surgical clips and the animal returned to its cage for monitoring.

After 21 days the animals were killed and the hindquarter removed. Radiological examination of the specimens was accomplished using a small parts X-Ray cabinet (Faxitron, Wheeling, Ill.). For quantization of bone formation, bone area and the bone mineral content (BMC) of an area of interest encompassing the site of ectopic bone formation was determined using a PIXImus2 small animal densitometer (GE Lunar, Madison, Wis.). Specimens were then placed in buffered formalin and submitted for routine processing for histological examination.

Various amounts of rhBMP-2 and BBP were combined and prepared for implantation. All possible combinations of the following amounts were used in pilot studies, rhBMP-2: 0 µg, 0.05 µg, 0.5 µg, 5 µg, and 50 µg; BBP: 0 µg, 50 µg, and µg 500 mg. Samples of 5 µg of rhBMP-2 were used in more extensive subsequent studies because that amount consistently produced an amount of ectopic bone that was neither too large nor too small for reliable analysis.

Results: BBP was tested alone and in combination with rhBMP-2.

FIG. 4 is a radiogram of mouse hind quarters 21 days after implantation of 500 µg of BBP in atelocollagen (top) or atelocollagen alone (bottom). When implanted alone with carrier, BBP induced calcification.

FIG. 5 is a histological section of mouse muscle 21 days after implantation of 500 µg of BBP in atelocollagen. Note the dystrophic calcification primarily associated with intramuscular adipose tissue. (H & E stain. Original magnification 100×.)

When 500 µg of BBP with sequence similarity to the TGF-β receptor II was implanted with 5 µg of rhBMP-2 the amount of ectopic bone formed, as measured by densitometry, was consistently greater than the amount of bone formed in animals into which identical amounts of the rhBMP-2 alone were implanted.

FIG. 6 are radiograms of mouse hind quarters 21 days after implantation of 5 µg of rhBMP-2 (left) or 5 µg of rhBMP-2 plus 500 mg of BBP (right). Note the increased opacity associated with the samples containing both rhBMP-2 and BBP.

Furthermore, implants that contained both the peptide and rhBMP-2 produced detectable cartilage and bone earlier than implants of BMP-2 alone.

FIG. 7 are radiograms of mouse hind quarters 9 (above) and 12 (below) days after implantation of 5 µg of rhBMP-2 (left) or 5 µg of rhBMP-2 plus 500 mg of BBP (right). Note the appearance of calcification in the sample from the day 9 sample containing both rhBMP-2 and BBP but not the sample containing BMP-2 alone.

Figure 8A:
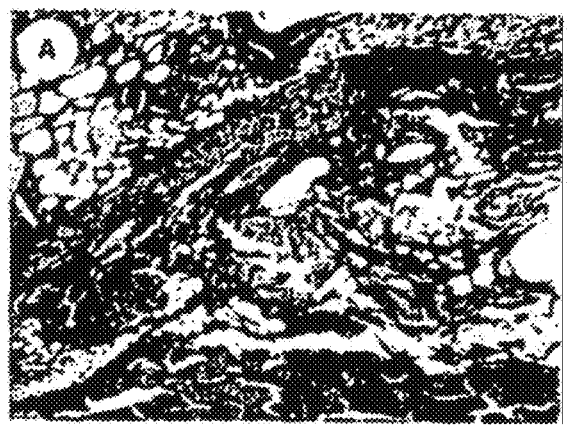
FIG. 8 are histological sections of mouse hind quarters 9 days after implantation of 5 μg of rhBMP-2 alone (A) or 5 μg of rhBMP-2 plus 500 μg of BBP (B).
Figure 8B:

FIG. 8 are histological sections of mouse hind quarters 9 days after implantation of 5 µg of rhBMP-2 alone (A) or 5 µg of rhBMP-2 plus 500 µg of BBP (B). Note the abundant cartilage in the BMP+BBP specimen whereas the BMP alone specimen shows the earlier stages of inflammation and mesodermal cell proliferation.

TABLE 2

Densitometric quantitation of ectopic bone formation with various amounts of BBP implanted with 5 µg of rhBMP-2. Mean, SE (n).

| | BBP (µg) | | |
|---|---|---|---|
| | 0 | 50 | 500 |
| Bone Area (cm$^2$) | 0.089 ± 0.0336 (12)* | 0.159 ± 0.0606 (8) | 0.226 ± 0.0270 (12)* |
| Bone Mineral Content (g) | 0.00189 ± 0.00084 (12)** | 0.00388 ± 0.0017 (8) | 0.00528 ± 0.00068 (12)** |

*p = 0.0044;
**p = 0.0049

Example 3

Surface Plasmon Resonance to Determine the Interaction of BMP-2 and the Synthetic Peptide Methods: The binding interaction between rhBMP-2 and BBP was characterized using surface plasmon resonance employing a Biacom X instrument (Biacore, Piscataway, N.J.). Buffers and chips for the procedure were obtained from Biacore. RhBMP-2 was dialyzed into 10 mM sodium acetate, pH 5.5 at a concentration of 1 mg/ml. This material was then attached to a CM-5 sensor chip using reagents and procedures supplied by the manufacturer. Running buffer was 10 mM HEPES, pH 7.4, 150 mM NaCl, 3 mM EDTA, 0.005% Surfactant P20. The peptide was dissolved in running buffer at concentrations ranging from $1\times10^{-5}$ to $1\times10^{-4}$ M. Flow rates from 5 to 50 µl/min and injection volumes of 20 to 100 µl were employed. The regeneration solution was 10 µM glycine-HCl, pH 2.0.

Results: Results of the surface plasmon resonance studies to determine the interaction between rhBMP-2 and BBP are shown in FIG. 9.

Figure 9:
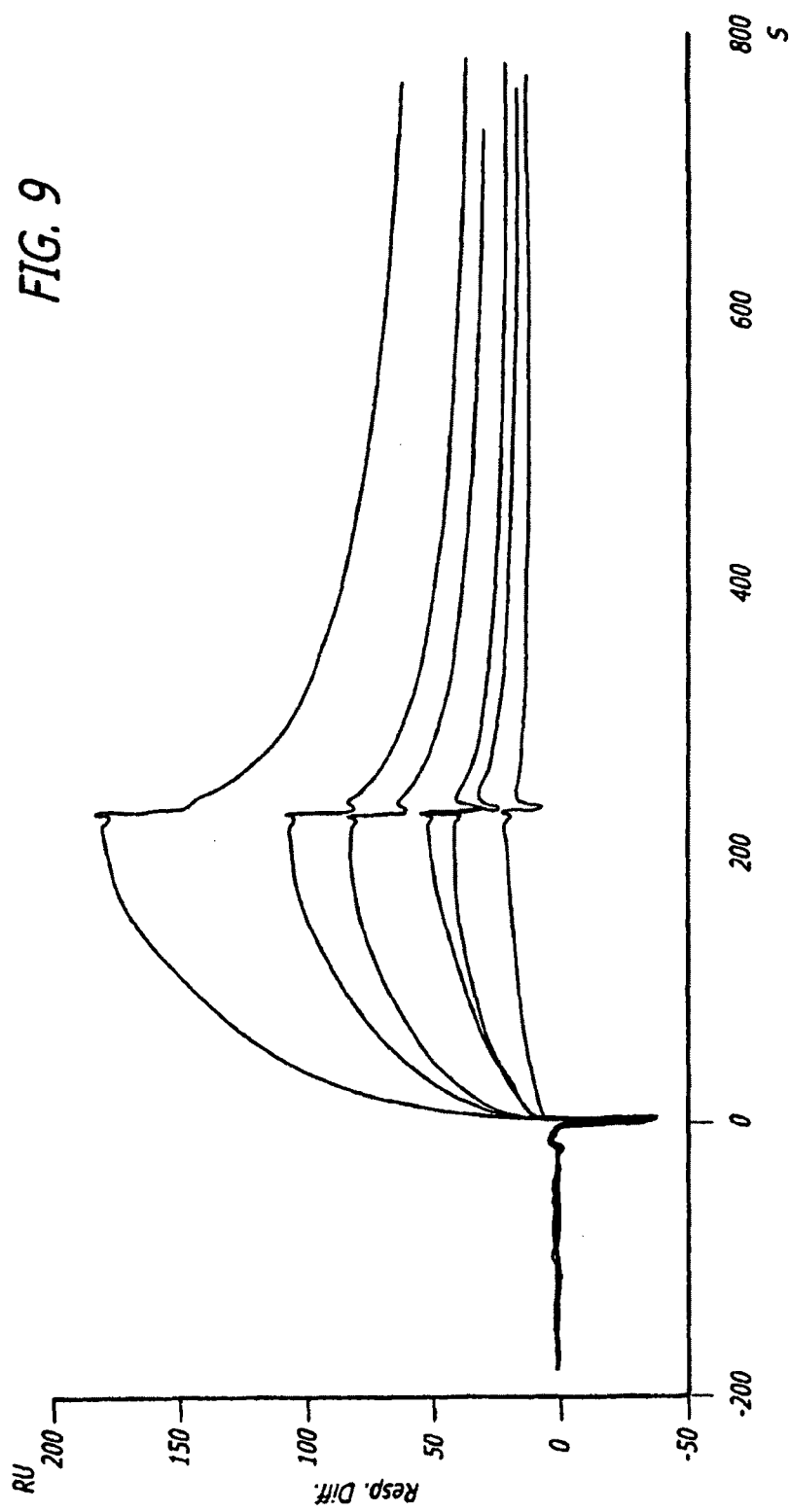
FIG. 9 is a surface plasmon resonance sensogram for the interaction of rhBMP-2 (affixed to the chip) and cyclized BBP at concentrations ranging from $1 \times 10^{-5}$ M $1 \times 10^{-4}$ M.

FIG. 9 is a surface plasmon resonance sensogram for the interaction of rhBMP-2 (affixed to the chip) and cyclized BBP at concentrations ranging from $1\times10^{-5}$ M $1\times10^{-4}$ M. The estimated dissociation constant ($K_D$) for the interaction was $3\times10^{-5}$ M. When the BBP was decyclized by prior reduction with β-mercaptoethanol, no significant binding occurred.

Example 4

Residence Time Study: BBP and rhBMP-2

Methods: Labeled rhBMP-2 was mixed with BBP or vehicle and applied to collagen sponges. The sponges were implanted into muscle pouches in rodents. At specified times (1, 3 and 7 days), the implants were removed and the amount of BMP remaining determined. Four animals were used in each group.

Results: BBP increased retention of rhBMP-2 by a factor of about two. FIG. 10 is a bar graph depicting the percentage of rhBMP-2 retention over 1, 3 and 7 days in the presence or absence of BBP.

Discussion: Increasing the retention of BMP at an implant site may improve the effectiveness of the BMP, and also reduce the amount required for the same therapeutic result.

While the specification describes particular embodiments of the present invention, those of ordinary skill can devise variations of the present invention without departing from the inventive concept.

Example 5

In Vivo Activity of Human BBP

Methods: The methods of Example 5 were utilized to test the activity of hBBP in eight mice in the hindquarter ectopic bone formation assay method using 5 µg rhBMP-2 alone (control) or 5 µg rhBMP-2 plus 0.05 mg human BBP (hBBP). After 4 weeks, the animals were killed and the hindquarter removed. X-ray and DEXA analysis were conducted.

Results: hBBP was tested in combination with rhBMP-2.

When implanted, hBBP with BMP resulted in a greater amount of calcification induction than BMP alone.

TABLE 3

Densitometric quantitation of ectopic bone formation with various amounts of BBP implanted with 5 µg of rhBMP-2. Mean, SE (n).

| Group | Mean BMC content (g) |
|---|---|
| rhBMP-2 (5 µg) | 0.00775 |
| hBBP (0.05 mg) + rhBMP-2 (5 µg) | 0.01125 |

Example 6

The Effect of BBP on Spinal Fusion as an Alternative of Adjunct to BMP in a Relevant Animal Model The rat posterior spinal fusion model was used to investigate the effect of BBP on fusion.

Methods: Three groups of 6 Lewis rats each underwent posterolateral intertransverse process spinal fusion at vertebrae L4-L5 with the application of collagen sponges containing: BBP (500 µg)(Group 1); BBP (500 µg) plus low-dose rhBMP-2 (1 µg) (Group 2); collagen plus low-dose rhBMP-2 (1 µg) (Group 3). Results were compared to historical controls of decortication only (0% fusion) and high-dose rhBMP-2 (3 µg)(100% fusion). All rats underwent post-operative radiography at 2, 4, 6, and 8 weeks. Manual spinal palpation was performed at 8 weeks, the time of sacrifice. Bone formation was assessed in histological sections stained with H&E.

Results: At week 8, the fusion rates were: 14% in Group 1 (BBP only); 80% in Group 2 (BBP plus low-dose BMP); and 40% in Group 3 (collagen plus low-dose BMP). This compares to 0% for historical negative controls at 100% for historical positive controls.

TABLE 4

Results of fusion rates by treatment group

| | Groups | | |
|---|---|---|---|
| | 1: BBP (500 µg) | 2. BBP (500 µg) + collagen plus low-dose rhBMP-2 (1 µg) | 3: collagen plus low-dose rhBMP-2 (1 µg) |
| Fusion Rates | 14% | 80% | 20% |

Discussion: Higher fusion rates in Group 2 (BBP plus low-dose BMP) as opposed to Group 3 (collagen plus low-dose BMP) suggest that BBP has an adjunctive effect on BMP that could permit the use of lower doses of BMP to achieve spinal fusion. Further studies with larger numbers of subjects are required to confirm these promising results.

Example 7

The Adjunctive Effect of a Binding Peptide on BMP in an Animal Spinal Fusion Model To investigate the effects of BBP on spinal fusion as an alternative or an adjunct to BMP in a relevant animal model.

Methods: Five groups of 50 Lewis rats each underwent posterolateral intertransverse process spinal fusion at vertebrae L4-L5 with implanted: BBP (500 µg) (Group 1); BBP (1000 µg) (Group 2), collagen plus low dose BMP-2 (1 µg) (Group 3), BBP (500 µg) plus low dose BMP (1 µg) (Group 4) and BBP (1000 µg) plus low dose BMP (1 µg) (Group 5). Control groups included a negative group (decortication) and positive control group (collagen plus 3 µg BMP).

All rats underwent post-operative radiography at 2, 4, 6, and 8 weeks. Manual spinal palpation was performed at 8 weeks, after the time of sacrifice. Bone formation was assessed in histological sections stained with H&E.

Results: At week 8, manual palpation of revealed 0% fusion with groups 1 and 2 (low d high dose BBP only), 40% fusion in group 3 and 90% fusion in groups 5 (BBP 1000 µg_low dose BMO). The difference between group 3 and 5 was close to statistical significance (p=0.056). Historical control groups as negative group (only decortation) resulted with a 0% fusion while the fusion rate with the positive control group (full dose BMP) was 100% in all our previous studies. The rate of radiographic fusion was significantly higher in group 5 than in group 3 at the 4th and 6th week (p<0.05) while it was nearly significant at the 8th week (p=0.056). Histological analysis revealed a more mature and thicker bone mass in group 4 and 5 when compared to group 3.

Discussion: Higher fusion rates with BBP plus low-dose BMP than collagen plus low-dose BMP may indicate an adjunctive effect of BBP on BMP possibly enabling the use of lower doses of BMP for spinal fusion in the future.

Example 8

The Adjunctive Effect of a Binding Peptide on BMP in an Animal Spinal Fusion Model A prospective 8 week interventional trial employing a rat model of spinal fusion to test the effect on bone morphogenetic protein binding peptide (BBP) on rhBMP-2 induced bone healing. The objective of this study was to determine if the addition of BBP to the collagen sponges used as a carrier for rhBMP-2 reduces the amount of rhBMP-2 required to achieve a satisfactory clinical outcome. BBP was effective as an adjunct to increase the effect of BMP-2 and enabled decreasing the dose of the protein necessary to provide fusion.

Methods: Posterolateral intertransverse process spinal fusion at L4-L5 was performed in five treatment groups of Lewis rats each, and collagen sponges (5×5×13 mm) were implanted into the surgical sites.

Each sponge was placed in a sterile microfuge tube and either a suspension of BBP (500 µg or 1000 µg) in water or sterile water alone was applied. The sponges were allowed to air dry in a tissue culture hood overnight and then placed at −70° C. for an hour and lyophilized overnight. The tubes (with small holes in the top to allow for lyophilization) were placed in autoclave pouches and sealed. The materials were then sterilized by exposure to chloroform vapor for at least 4 hours. Immediately prior to surgery, the pouches were opened and the sponges were removed from the tubes and placed in a second tube containing the designed amount of rhBMP-2 or water. The sponges were able to completely absorb the solution.

The posterolateral intertransverse process spinal fusion at L4-L5 in the rat is a well established procedure in our laboratory 13-17. Briefly, the animal was anesthetized with isofluane and the surgical site was shaved and prepped with Betadyne and alcohol. A 3 cm longitudinal midline incision was made through the skin and subcutaneous tissue over L4-L5 down to the lumbodorsal fascia. Then, two separate 2 cm longitudinal paramedial incisions were made in the erector spinae muscles on both sides of L4-L5. The transverse processes of L4-L5 were exposed, cleaned of soft tissue, and decorticated with a high-speed burr. The site was irrigated with saline and the therapeutic test material was placed. The lumbodorsal fascia was closed with 4-0 Prolene (Ethicon, Somerville, N.J.). The skin was closed with 4-0 Prolene and meticulous post-operative care was provided.

Two doses of BBP (500 µg, and 1000 µg) were tested with or without "low dose" (1 µg) rhBMP-2 and the results were compared to the low dose (1 µg) rhBMP-2. These were compared to control groups. Fusion was evaluated by radiology, histology and manual palpation tests. Animals were sacrificed 8 weeks after surgery.

The results of the surgeries were assessed radiologically, histologically, and by manual palpation. Posteroanterior radiographs were obtained using a small parts X-ray cabinet (Faxitron Corp., Wheeling, Ill.) on each animal at 2, 4, 6 and 8 weeks. Radiograms were evaluated by three independent observers employing the following standardized scale: 0: no fusion; 1: incomplete fusion with bone formation present; and 2: complete fusion. The scores from the three observes were added and a total of 5 or 6 was regarded as "fused". Manual palpation of the spine was performed at the time of sacrifice at 8 weeks. To simulate the gold standard for determining fusion in humans, exploration and manual palpation of the fusion mass were performed after death. The level fused was manually palpated with Adson forceps and compared with the adjacent nonfused levels. Each specimen was graded as fused or non-fused by three independent observers. The spine was designated as "not fused" if any of the three observers graded the spine as not fused. After manual palpation, the specimens were decalcified using standard 10% decalcifying solution HCl (Cal-Ex, Fisher Scientific, Fairlawn, N.J.), washed with running tap water, then transferred to 75% ethanol. Sagittal sections were cut carefully at the level of the transverse process. The specimens were imbedded in paraffin and sections of each specimen obtained. These sections were stained with hematoxylin and eosin. They were evaluated by an independent observer as fused and not fused.

The proportions of subjects in each group judged to be "fused" were compared in sequential two group comparisons with Fisher's exact test using SPSS software. A p score of less than or equal to 0.05 was set for statistical significance.

Results: Radiology revealed significant earlier fusion with 1000 µg BBP+1 µg BMP-2. combination when compared to low dose BMP-2 (1 µg) only ($p<0.05$). Manual palpation and histology at 8th week revealed higher rate of fusion with the same combination with a nearly significant difference ($p=0.057$).

TABLE 5

Results of radiological examination

| | Week | | | |
|---|---|---|---|---|
| | 2nd (%) | 4th (%) | 6th (%) | 8th (%) |
| Group 1: low dose BBP only (500 µg) | 0 | 0 | 0 | 0 |
| Group 2: high dose BBP only (1000 µg) | 0 | 0 | 0 | 0 |
| Group 3: low dose BMP-2 only (1 µg rhBMP-2) | 0 | 20 | 30 | 40 |
| Group 4: low dose BBP + low dose BMP-2 | 0 | 20 | 80 | 80 |
| Group 5: high dose BBP + low dose BMP-2 | 40 | 80 | 90 | 90 |
| Group 6: decortication only | — | — | — | 0 |
| Group 7: high dose BMP-2 only (10 µg rhBMP-2) | — | — | — | 100 |

TABLE 6

Results of manual palpation and histology at 8th week.

| | Histology (%) | Manual Palpation (%) |
|---|---|---|
| Group 1: low dose BBP only (500 µg) | 0 | 0 |
| Group 2: high dose BBP only (1000 µg) | 0 | 0 |
| Group 3: low dose BMP-2 only (1 µg rhBMP-2) | 40 | 40 |
| Group 4: low dose BBP + low dose BMP-2 | 80 | 80 |
| Group 5: high dose BBP + low dose BMP-2 | 90 | 90 |
| Group 6: decortication only | — | — |
| Group 7: high dose BMP-2 only | — | 100 |

Figure 15:
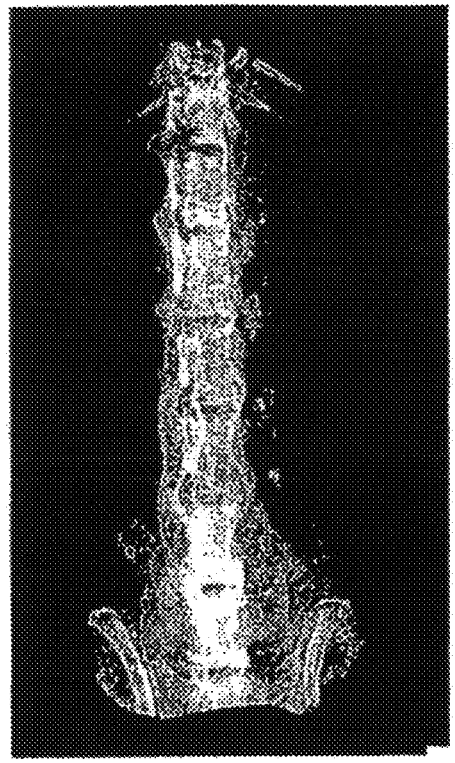
FIG. 15 is an anterior-posterior radiograph of a rat spine fused at L4-L5 with the application of BBP high dose (1000 μg)+rhBMP-2 low dose (1 μg) 8 weeks after treatment.
Figure 16:
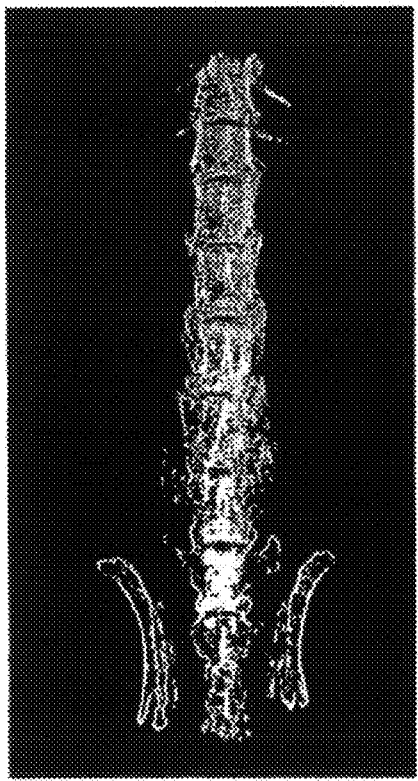
FIG. 16 is an anterior-posterior radiograph of a rat spine showing pseudoarthritis at right anno fusion at left L4-L5 with the application of rhBMP-2 (1 μg) treatment.

The results of the radiological examinations are shown in Table 5 which presents the proportion of subjects in each group that had a score of 5 or 6 and was, therefore, judged to be "fused" for each of the four time points (2, 4, 6 and 8 weeks). As can be seen none of the animals in low and high dose BBP groups developed fusion at any time points. Low dose BBP+low dose BMP-2 group had a higher fusion rate than BMP-2 low dose only group at the 6th and 8th weeks and this difference was significant (p<0.05) for the 6th week while not significant at the 8th week (p=0.170). On the other hand BBP high dose+BMP-2 low dose group had a significantly higher fusion rate at the 4, 6 and 8 week time points when compared to BMP-2 low dose only group (p<0.05 for each time point) (FIGS. 15 and 16).

Figure 17:
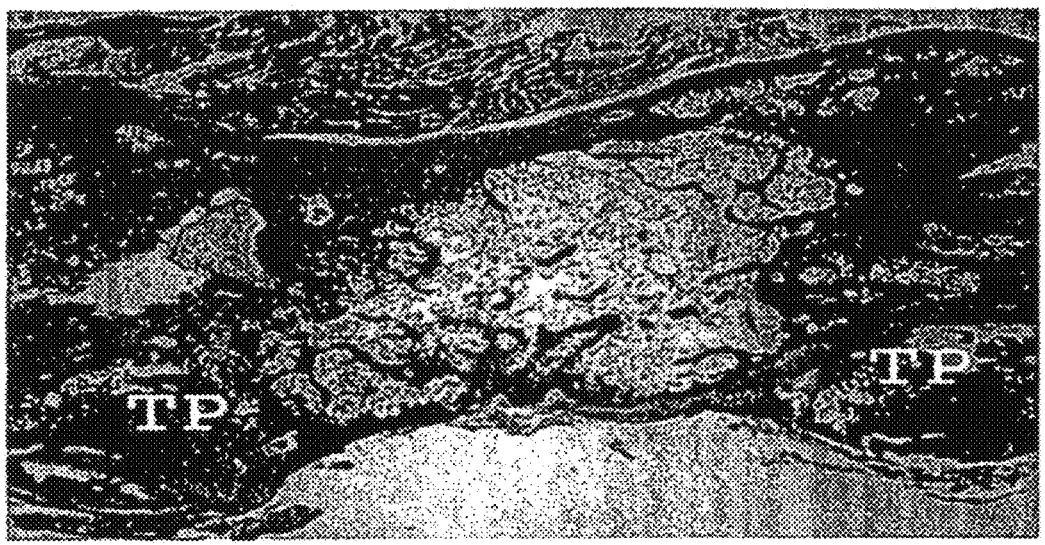
FIG. 17 is a histological section of rat spinal region 8 weeks after treatment of a combination of BBP and rhBMP-2. (H & E stain. Original magnification 8.4×.)
Figure 18:
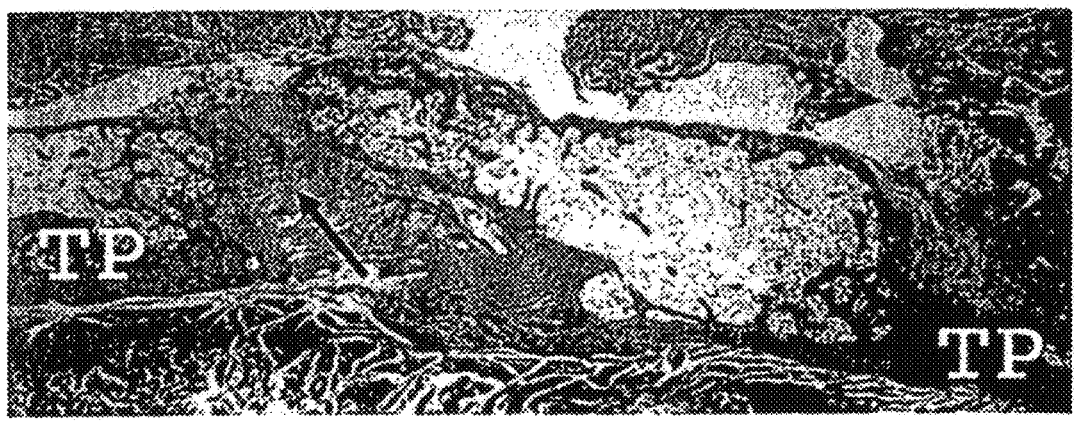
FIG. 18 is a histological section of rat spinal region 8 weeks after treatment with low dose rhBMP-2 (1 μg). (H & E stain. Original magnification 8.4×.)

Table 6 shows the proportions of subjects in each group judged to be "fused" by three independent clinical evaluators. The critical comparison was between BMP-2 low dose group versus BBP low dose+BMP-2 low dose and BBP high dose+BMP-2 low dose groups. The fusion rate assessed by manual palpation was higher in both combination groups when compared to BMP-2 low dose group (FIGS. 15 and 16). However, this difference was not significant while it tended towards significance for the comparison of BBP high dose+BMP-2 low dose group with BMP-2 low dose group (p=0.057). The thickness of the fusion mass tended to be thicker and the maturity of the bone tended to be more mature in the specimens of the fused combination groups when compared to the specimens of the fused low dose BMP-2 group (FIGS. 17 and 18). FIG. 17 is a histological section of rat spinal region 8 weeks after treatment of a combination of BBP and rhBMP-2 showing thick fusion mass between L4 and L5 transverse process with cortical-matured bone. (H & E stain. Original magnification 8.4×). FIG. 18 is a histological section of rat spinal region 8 weeks after treatment with low dose rhBMP-2 (1 µg) showing immature bone bridging the cortical matured bridging bony parts. (H & E stain. Original magnification 8.4×).

Table 6 also shows the proportion of subjects in each group judged to be fused by an independent histologist. The results confirmed the results of both the manual palpation and radiology at the 8th week demonstrating the similar fusion rates. The thickness of the fusion mass tended to be thicker and the maturity of the bone tended to be more mature in the specimens of the fused combination groups when compared to the specimens of the fused low dose BMP-2 group (FIGS. 17 and 18).

Specific growth factor binding agents, such as BBP, can be compounded into carriers used in fusion procedures to decrease the dosage of BMP and possibly decrease the side effects which are most likely dose-related. This may also decrease costs and improve clinical outcomes.

The radiographic results demonstrated significantly higher and earlier fusion rates with high dose BBP+low dose BMP-2 combination when compared to the same amount of the protein in its single use. The histology and the manual palpation tests confirmed this higher rate of fusion at the 8th week with a nearly significant difference. It is important to note that this model of spinal fusion is difficult to fuse and requires a material with significant osteoinductive ability to induce a solid arthrodesis. Likewise, use of either 500 µg or 1000 µg BBP alone did not provide fusion in the spinal model, while there was ectopic dystrophic calcification formation with 500 µg BBP implantation in the muscle pouch model. In the histological examination, we have observed a more mature bone fusion mass with the combination groups when compared with the BMP-2 only group (FIGS. 17 and 18).

We claim:

1. A method of increasing the rate of bone formation in vertebrate tissue, comprising applying to the tissue a peptide having the sequence of SEQ ID NO: 11, or a fragment thereof, and a close of least one bone growth factor, wherein said peptide or fragment increases the rate of bone growth, and wherein the combination results in a faster rate of bone formation than treatment with the same dose of the at least one bone growth factor alone.

2. The method of claim 1 wherein the bone growth factor is a TGF-β family member.

3. The method of claim 1 wherein the bone growth factor is selected from the group comprising: TGF-β, BMP-2, BMP-3, BMP-4, BMP-6, BMP-7, BMP-8, BMP-9, GDF5 and demineralized bone matrix.

4. The method of claim 1 wherein the peptide has the sequence of SEQ. ID NO: 1, and the bone growth factor is a BMP.

5. The method of claim 1 wherein the peptide has the sequence of SEQ. ID NO: 12, and the bone growth factor is a hBMP.

6. The method of claim 1 wherein bone formation is measured as ostegenesis.

7. The method of claim 1 wherein bone formation is measured by calcification.

8. A method of increasing the rate of vertebrate bone fusion, comprising applying to a tissue a peptide having the sequence of SEQ ID NO: 11, or a fragment thereof, wherein said peptide or fragment increases the rate of bone fusion, and a dose of least one bone growth factor, wherein the combination results in a faster rate of bone fusion than treatment with the same dose of the at least one bone growth factor alone.

9. The method of claim 8 wherein the bone growth factor is a TGF-β family member.

10. The method of claim 8 wherein the bone growth factor is selected from the group comprising: TGF-β, BMP-2, BMP-3, BMP-4, BMP-5, BMP-6, BMP-7, BMP-8, BMP-9, GDF5 and demineralized bone matrix.

11. The method of claim 8 wherein the peptide has the sequence of SEQ. ID NO: 1, and the bone growth factor is a BMP.

12. The method of claim 8 wherein the peptide has the sequence of SEQ. ID NO: 12, and the bone growth factor is a hBMP.

13. A method of inducing vertebrate bone fusion, comprising applying to a tissue a peptide having the sequence of SEQ ID NO: 11, or a fragment thereof, wherein said peptide or fragment induces bone fusion, and a dose of least one bone growth factor.

14. The method of claim 13 wherein the bone growth factor is a TGF-β family member.

15. The method of claim 13 wherein the bone growth factor is selected from the group comprising: TGF-β, BMP-2, BMP-3, BMP-4, BMP-5, BMP-6, BMP-7, BMP-8, BMP-9, GDF5 and demineralized bone matrix.

16. The method of claim 13 wherein the peptide has the sequence of SEQ. ID NO: 1, and the bone growth factor is a BMP.

17. The method of claim 13 wherein the peptide has the sequence of SEQ. ID NO: 12, and the bone growth factor is a hBMP.

18. A method of inducing membranous bone formation, comprising applying to a tissue proximate to membranous bone, a peptide having the sequence of SEQ ID NO: 11, or a fragment thereof, wherein said peptide or fragment induces membranous bone formation, and a dose of least one bone growth factor, wherein the combination results in a greater degree of membranous bone formation than treatment with the same dose of the at least one bone growth factor alone.

19. The method of claim 18 wherein the bone growth factor is a TGF-β family member.

20. The method of claim 18 wherein the bone growth factor is selected from the group comprising: TGF-β, BMP-2, BMP-3, BMP-4, BMP-5, BMP-6, BMP-7, BMP-8, BMP-9, GDF5 and demineralized bone matrix.

21. The method of claim 18 wherein the peptide has the sequence of SEQ. ID-NO: 1, and the bone growth factor is a BMP.

22. The method of claim 18 wherein the peptide has the sequence of SEQ. ID NO: 12, and the bone growth factor is a hBMP.

* * * * *

UNITED STATES PATENT AND TRADEMARK OFFICE
CERTIFICATE OF CORRECTION

| | | |
|---|---|---|
| PATENT NO. | : 8,415,302 B2 | Page 1 of 1 |
| APPLICATION NO. | : 12/448497 | |
| DATED | : April 9, 2013 | |
| INVENTOR(S) | : Murray et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 184 days.

Signed and Sealed this
Sixteenth Day of December, 2014

Michelle K. Lee
*Deputy Director of the United States Patent and Trademark Office*